(12) United States Patent
Auner et al.

(10) Patent No.: US 7,043,129 B2
(45) Date of Patent: May 9, 2006

(54) WIDE BANDGAP SEMICONDUCTOR WAVEGUIDE STRUCTURES

(75) Inventors: Gregory W. Auner, Livonia, MI (US); Mona R. Safadi, Grosse Pointe Park, MI (US)

(73) Assignee: Wayne State University, Detroit, MI (US)

( * ) Notice: Subject to any disclaimer, the term of this patent is extended or adjusted under 35 U.S.C. 154(b) by 286 days.

(21) Appl. No.: 10/353,757

(22) Filed: Jan. 28, 2003

(65) Prior Publication Data

US 2004/0146264 A1 Jul. 29, 2004

Related U.S. Application Data

(63) Continuation of application No. 10/125,031, filed on Apr. 17, 2002, now Pat. No. 6,848,295.
(60) Provisional application No. 60/212,214, filed on Jun. 16, 2000.

(30) Foreign Application Priority Data

Jun. 15, 2001 (WO) .............................. PCT/WO01/97899

(51) Int. Cl.
*G02B 6/10* (2006.01)

(52) U.S. Cl. ..................... 385/130; 385/129; 385/14; 385/141
(58) Field of Classification Search .................. 385/14, 385/129, 130, 131, 132, 141
See application file for complete search history.

(56) References Cited

U.S. PATENT DOCUMENTS

| 4,189,516 A | 2/1980 | Dryburgh et al. ........... 428/409 |
| 4,265,124 A | 5/1981 | Lim et al. ...................... 73/703 |
| 4,511,816 A | 4/1985 | Mikoshiba et al. ..... 310/313 A |
| 4,937,454 A | 6/1990 | Itoh et al. .............. 250/370.11 |
| 5,109,844 A | 5/1992 | de Juan, Jr. et al. ..... 528/419 R |

(Continued)

OTHER PUBLICATIONS

International Search Report to International Application PCT/US03/11863.
International Search Report to International Application PCT/US03/11775.
International Search Report to International Application PCT/US03/11773.
Thompson, D.F. et al., "Surface Transverse Wave Propagation Under Metal Strip Gratings", Proc. IEEE Ultrasonic Symp., Nov. 1986, 261–265.
D.S. Ballantine et al., "Acoustic Wave Sensor—Theory, Design, and Physico–Chemical Applications", *Academic Press* (1997).
C. Caliendo et al., "Piezoelectric AlN Film for SAW Device Applications", Proc. IEEE Ultrasonic Symp., 249–252 (1992).
K. Kaya et al., "Synthesis of AlN Thin Films on Sapphire Substrates by Chemical Vapor Deposition of $AlCl_3$—$NH_3$ Systems and Surface Acoustic Wave Properties", *Jpn. J. Appl. Phys.*, vol. 35, 2782–2787, (1996).
G. Carlotti et al., "The Elastic Constants of Sputtered AlN Films", Proc. IEEE Ultrasonic Symp., 353, (1992).
R.L. Baer et al., "STW Chemical Sensors", Proc. IEEE Ultrasonic Symp., 293–298 (1992).

(Continued)

*Primary Examiner*—Brian M. Healy
(74) *Attorney, Agent, or Firm*—Kenyon & Kenyon

(57) ABSTRACT

A waveguide structure for transmitting broad spectrum light, includes a wide bandgap semiconductor thin film arranged on a substrate and ablated to form a waveguide channel to transmit the broad spectrum light.

10 Claims, 28 Drawing Sheets

U.S. PATENT DOCUMENTS

| | | | |
|---|---|---|---|
| 5,155,364 A | 10/1992 | Fujii | 250/364 |
| 5,229,569 A | 7/1993 | Miyauchi et al. | 219/121.6 |
| 5,343,107 A | 8/1994 | Shikata et al. | 310/313 A |
| 5,354,980 A | 10/1994 | Rappoport et al. | 250/208.1 |
| 5,385,862 A | 1/1995 | Moustakas | 437/107 |
| 5,456,797 A | 10/1995 | Weber et al. | 437/67 |
| 5,464,984 A | 11/1995 | Cox et al. | 250/370.11 |
| 5,510,481 A | 4/1996 | Bednarski et al. | 536/120 |
| 5,677,538 A | 10/1997 | Moustakas et al. | 250/370.12 |
| 5,935,155 A | 8/1999 | Humayun et al. | 607/54 |
| 5,936,247 A | 8/1999 | Lange et al. | 250/363.03 |
| 5,944,747 A | 8/1999 | Greenberg et al. | 607/54 |
| 5,992,215 A | 11/1999 | Caron et al. | 73/24.01 |
| 6,084,503 A | 7/2000 | Ruile et al. | 340/10.1 |
| 6,137,231 A | 10/2000 | Anders et al. | 315/111.21 |
| 6,144,332 A | 11/2000 | Reindl et al. | 342/42 |
| 6,243,517 B1 | 6/2001 | Deacon | 52/582.2 |
| 6,282,357 B1 | 8/2001 | Kadota et al. | 385/129 |
| 6,312,568 B1 | 11/2001 | Wilke et al. | 204/192.18 |
| 6,450,008 B1 | 9/2002 | Sunshine et al. | 73/23.34 |
| 6,501,107 B1 | 12/2002 | Sinclair et al. | 257/209 |
| 6,518,637 B1 | 2/2003 | Thompson et al. | 257/416 |
| 6,567,753 B1 | 5/2003 | Potyrailo | 702/39 |
| 2001/0054305 A1 | 12/2001 | Banda et al. | 73/24.01 |
| 2002/0008191 A1 | 1/2002 | Faska et al. | 250/208.1 |
| 2003/0052701 A1 | 3/2003 | Brown et al. | 250/208.1 |
| 2003/0127044 A1 * | 7/2003 | Schowalter et al. | 117/106 |
| 2003/0156812 A1 * | 8/2003 | Farah et al. | 385/129 |
| 2003/0186479 A1 * | 10/2003 | Kim et al. | 438/46 |
| 2003/0196477 A1 * | 10/2003 | Auner et al. | 73/24.06 |
| 2004/0099870 A1 * | 5/2004 | Ono et al. | 257/79 |
| 2004/0145053 A1 * | 7/2004 | Auner et al. | 257/737 |
| 2004/0146264 A1 * | 7/2004 | Auner et al. | 385/130 |

OTHER PUBLICATIONS

R.M. White, "Surface Elastic Waves" *Proc. IEEE*, 58, 1238–1276 (1970).

B.A. Auld et al., "Surface Transverse Wave Propagation Under Metal Strip Gratings", *Proc. IEEE Ultrasonic Symp.*, 261, (1986).

C. Campbell, "Surface Acoustic Wave Devices and Their Signal Processing Applications", *Academic Press Inc.*, (1989) (Chapter 18).

M.P. Thompson et al., "Epitaxial Growth of Zinc–Blende AlN on SI (001) Substrates by Plasma Source Molecular Beam Epitaxy", *Proceedings of Spring Materials Research Society, San Francisco, CA*, vol. 570, pp. 297–302 (1999).

G.W. Auner et al., "Microstructure of Low temperature grown AlN thin films on Si (III)" *J. Appl. Phys.*, 85, 7879 (1999).

S. Ballandras et al., "New Results on Surface Transverse Wave Resonators Built with Different Combinations of Groove and Strip Gratings", *IEEE Ultrasonic Symp. Proc.*, 217, 1998.

L.J. Patgridge, "Production of Catalytic Antibodies Using Combinatorial Libraries", *Biochem Soc Trans.*, 21(4), 1096 (1993).

P.K. Kuo et al., "Generation of a Large Combinatorial Library of the Immunoglobulin Repertoire in Phage Lambda", *Science*, 246, 1275 (1989).

M. Tom–Moy et al., "Atrazine Measurements Using Surface Transverse Wave Devices", *Anal. Chem., 1510–1516*, (1995).

Zhao, Q. et al., "Development of Wide Bandgap Semiconductor Photonic Device Structures By Excimer Laser Micromachining", *MRS Internet J. Nitride Semicond. Res.*, 5S1, W11.69 (2000).

Auner, G.W., et al., "Characterization of Aluminum Nitride Thin Films Grown by Plasma Source Molecular Beam Epitaxy", 362, *SPIE* vol. 2428.

Krupitskaya, R.Y. "Optical Characterization of AlN Films Grown by Plasma Source Molecular Beam Epitaxy", *J. Appl. Phys.*, vol. 84(5), 2861, (1998).

Ed. Devices, J.H., and Long, A.R., "Physics of Nanostructure," *Institute of Physics Publishing, Philadelphia*, 1992.

Gourley, P.L., "Nanolasers," *Scientific American*, Mar. 1998.

Zhao, Q., et al., "Development of Wide Band Gap Semiconfuctor Photonic Device Structures by Excimer Laser Micromachining." *Mat. Res. Soc. Proceedings*, vol. 595, W11.69.1, 2000.

P.K. Kuo. G.W. Auner and Z.L. Wu,"Microstructure and thermal conductivity of epitaxial AlN thin films" *Thin Film Solids*, 253, 223 (1994).

G.W. Auner, et al., "Epitaxial Growth of AlN by Plasma Source Molecular Beam Epitaxy" in Wide Bandgap Electronic Materials, (edited by M.A. Prelas), 329–334, (Kluwer Academic Publishers, 1995).

J. Rizzo and J. Wyatt, "Prospects for a Visual Prosthesis", *The Neuroscientist*, vol. 3, No. 4 (1997).

Oh, S.H., et al., "Comparative Kinetic Studies of $CO-O_2$ and CO–NO Reactions over Single Crystal and Supported Rhodium Catalysts," *J. Catalysis*, 100, 360, 1986.

Ng, K.Y.S., et al., "NO–CO Activity and Selectivity over a $Pt_{10}Rh_{90}(111)$ Alloy Catalyst in the 10–torr Pressure Range," *J. Catalyis*, 146, 349, 1994.

Cox, D.M., et al., "Gold Clusters—Reactions and Deuterium Uptake" *Zeitschirift Fur Physik D–Atoms Molecules and Clusters*, vol. 19 (1–4), 353, 1991.

Heiz, U., et al., "CO Chemisorption on Monodispersed Platinum Clusters on $SiO2$ Detection of CO Chemisorption on Single Platinum Atoms," *Journal of Physical Chemistry*, 99(21), 8730, 1995.

Haruta, M., "Size–and–support–dependency in the catalysis of gold," *Catalysis Today*, 36(1), 153, 1997.

Chianelli, R.R., et al., "Synthesis, Fundamental Properties and Applications of Nancrystals, Sheets, Nanotubes, and Cylinders based on Layered Transition Metal Chalcogenides," *Materials Technology*, 15(1), 35–84, 2000.

Chianelli, R.R., et al., "Fundamental Studies of Transition–metal Sulfide Catalytic Materials," *Advances in Catalysis*, 40, 177, 1994.

Reetz, M.T., et al., "Visualization of Surfactants on Nanostructured Palladium Clusters by a Combination of STM and High–resolution TEM," *Science*, vol. 267, pp. 367–369, 1995.

Xu,H., and Ng, K.Y.S., "STM Study of Oxygen on Rh(111)." *Surface Science*, 375, 161, 1997.

Serina, F., et al., Pd/AlN/SiC thin–film devices for selective hydrogen sensing AP, *Apl. Phys. Lett.*, 79 (20): 3350–3352(2001).

Serina, F., et al., Pd/AlN/Si or SiC Structure for Hydrogen Sensing Device, *Mat. Res. Soc. Symp.*, vol. 622, Ti.3.1 (2000).

Kryder M.H., "Ultra high density recording technologies," *MRS Bull.*, vol. 21, (9), 17 (1996).

Chou, S., et al., "Nanolithographically defined magnetic structures and quantum magnetic disk", *J. Appl. Phys.*, 79, 6101 (1996).

Leslie–Pelecky, D.L. and Rieke, R.D., "Magnetic Properties Nanostructured Materials" *Chem. Mater.*, 8, 1770–1783, 1996.

Wittborn, J., et al., Magnetic domain and domain wall imaging of submicron Co dots by probing the magnetostrictive response using atomic force microscopy, *Appl. Phys. Lett.*, vol. 76, No., 20 2931 (2000).

* cited by examiner

WIDE BANDGAP SEMICONDUCTOR WAVEGUIDE STRUCTURES

RELATED APPLICATION INFORMATION

This application claims the benefit of and priority to U.S. patent application Ser. No. 10/125,031, entitled "Apparatus, Method and System for Acoustic Wave Sensors Based on AlN Thin Films", filed Apr. 17, 2002, now U.S. Pat. No. 6,848,295, the disclosure of which is incorporated by reference in its entirety herein.

This application claims the benefit of U.S. Patent Application Ser. No. 60/212,214, entitled "Method and Apparatus for Stimulating Neurological Tissue", filed Jun. 16, 2000, the disclosure of which is incorporated by reference in its entirety herein, and corresponding PCT Application No. WO 01/97899, filed on Jun. 15, 2001 and published on Dec. 27, 2001, the disclosure of which is also incorporated by reference in its entirety herein.

FIELD OF THE INVENTION

The present invention relates to broad-spectrum waveguide structures formed from wide bandgap semiconductor thin films and a method to make such structures.

BACKGROUND INFORMATION

The development of functional broad-spectrum waveguide structures from wide bandgap semiconductor materials may remain difficult due to their immunity to many processing technologies. It is believed that other prior systems may use only hot Potassium Hydroxide and certain energetic plasma techniques to form aluminum nitride (AlN) based device structures. However, such processes may not be adequately controlled and/or may produce damaged structures so that a better approach may be needed.

In addition, there may be a need for a waveguide structure that may be used in physiological drug delivery systems, which may use "caged" neurotransmitter substances to stimulate retinal and cortical tissue.

SUMMARY OF THE INVENTION

An exemplary embodiment and/or exemplary method of the present invention may provide a broad-spectrum optical waveguide structure formed from wide bandgap semiconductor materials, such as, for example, aluminum nitride (AlN). The use of wide bandgap semiconductors materials may provide high quality waveguide structures because such materials may possess a near atomically smooth topology and may be fabricated to transmit light from a broad spectrum, including for example, light within the infrared to ultraviolet (UV) range.

The exemplary embodiments and/or exemplary methods involve using a deposition method of plasma source molecular beam epitaxy (PSMBE) to prepare the wide bandgap semiconductors at low temperatures, including, for example, an aluminum nitride (AlN) semiconductor thin film deposited on a sapphire substrate. The plasma source molecular beam epitaxy (PSMBE) deposition method may include the use of a magnetically enhanced hollow cathode deposition source for growing the wide bandgap semiconductors.

The exemplary embodiments and/or exemplary methods also involve using an excited dimmer (Excimer) laser micromachining arrangement to fabricate waveguide structures from the wide bandgap semiconductors deposited by the plasma source molecular beam epitaxy (PSMBE) system. A 248 nanometer KrF Excimer laser, for example, may be applied to a single crystal wide bandgap semiconductor thin film to fabricate the wave-guiding channels.

The broad-spectrum waveguide structures of the present invention may be used for a variety of applications that require a uniform transmission in the range of, for example, 5 microns to 750 nanometers. In particular, the exemplary broad-spectrum waveguide structures may be used to spatially deliver deep ultraviolet (UV) light for biomedical applications, or broad-spectrum infrared to ultraviolet (UV) light for miniaturized spectrometer applications.

The exemplary waveguide structure may be used in a variety of applications, both chemical and medical, including, for example, a physiological drug delivery system and spectroscopy.

According to one exemplary application of the waveguide structure, a spatial and temporal drug delivery may be provided within the retina by delivering ultraviolet (UV) light in precise intensities to selective areas of a microfluidic implant without direct ultraviolet (UV) exposure to the biological cells in retinal and cortical implants. In particular, the exemplary waveguide structures may be applied in a microfluidic retinal prosthesis described in U.S. patent application Ser. No. 60/212,214, entitled "Method and Apparatus for Stimulating Neurological Tissue" ("the Iezzi patent"), filed Jun. 16, 2000, the disclosure of which is incorporated by reference in its entirety herein, to facilitate spatial and quantitative photoactivation of "caged" neurotransmitters to microfluidic channels. Physiological drug delivery systems, such as the microfluidic retinal prothesis described in the Iezzi patent, may require a waveguide capable of deep ultraviolet light transmission for the activation of the caged neurotransmitters. Hence, physiological drug delivery systems may benefit from the exemplary broad-spectrum waveguides of the present invention, which may transmit light, for example, in the 360 nanometer range.

An exemplary waveguide structure may also be applied in the area of spectroscopy to provide a broad-spectrum photonic waveguide for use in the development of a miniaturized spectrometer system arranged, for example, on a microchip. The applied exemplary waveguide may transmit light within the 5000 nanometers to 250 nanometer range, which may be critical for many chemical analysis applications, including, for example, a miniature Raman Spectroscopy system.

An exemplary embodiment and/or exemplary method is directed to a waveguide structure for transmitting broad spectrum light including a wide bandgap semiconductor thin film arranged on a substrate and ablated to form a waveguide channel to transmit the broad spectrum light.

Another exemplary embodiment and/or exemplary method is directed to providing the waveguide structure, in which the broad spectrum light includes ultraviolet light and infrared light.

Yet another exemplary embodiment and/or exemplary method is directed to providing the waveguide structure, in which the broad spectrum light includes light with a range of 5 microns to 750 nanometers.

Still another exemplary embodiment and/or exemplary method is directed to providing the waveguide structure, in which the wide bandgap semiconductor thin film includes aluminum nitride and the substrate includes sapphire.

Yet another exemplary embodiment and/or exemplary method is directed to providing the waveguide structure, in which the waveguide channel is approximately 5 μm to 50 μm wide.

Still another exemplary embodiment and/or exemplary method is directed to providing the waveguide structure, further including a termination hole for the light to exit the waveguide structure.

Yet another exemplary embodiment and/or exemplary method is directed to providing the waveguide structure, further including a pixelated array of termination holes to direct the broad spectrum light.

Still another exemplary embodiment and/or exemplary method is directed to providing a waveguide structure for transmitting broad spectrum light for use with a physiological delivery system, including a wide bandgap semiconductor thin film arranged on a substrate and ablated to form a waveguide channel to transmit the broad spectrum light, in which the waveguide structure is integrated with the physiological drug delivery system.

Yet another exemplary embodiment and/or exemplary method is directed to providing the waveguide structure, in which the physiological drug delivery system includes a microfluidic retinal prosthesis.

Still another exemplary embodiment and/or exemplary method is directed to providing a waveguide structure for transmitting broad spectrum light for use with a miniaturized spectrometer system, including a wide bandgap semiconductor thin film arranged on a substrate and ablated to form a waveguide channel to transmit the broad spectrum light, in which the waveguide structure is arranged to transmit light to the miniaturized spectrometer system.

Yet another exemplary embodiment and/or exemplary method is directed to providing a fabrication of a broad spectrum waveguide structure, including depositing a wide bandgap semiconductor thin film onto a substrate, and micro-machining the deposited wide bandgap semiconductor thin film to form a waveguide channel.

Still another exemplary embodiment and/or exemplary method is directed to providing a fabrication of the broad spectrum waveguide structure, in which the wide bandgap semiconductor thin film includes aluminum nitride and the substrate includes sapphire.

Yet another exemplary embodiment and/or exemplary method is directed to providing a fabrication of a broad spectrum waveguide structure, in which the depositing of the wide bandgap semiconductor thin film further includes cleaning ultrasonically the substrate using at least one of acetone and methanol, etching the substrate in an acidic mixture, pressuring an ultra high vacuum chamber of a plasma source molecular beam epitaxy system to a base vacuum pressure, loading the substrate into the ultra-high vacuum chamber, heating the substrate to a temperature of about 800° C., operating an impeller of the plasma source beam epitaxy system to accelerate ions, maintaining an energy level half that of a deposited crystal displacement energy, maintaining a temperature of at least one of 400° C. and 650° C. during deposition, and rotating the substrate at a temperature of 650° C. for final growth of the wide bandgap semiconductor thin film.

Still another exemplary embodiment and/or exemplary method is directed to providing a fabrication of a broad spectrum waveguide structure, in which the base vacuum pressure is $1\times10^{-10}$ Torr, a supplied power is 200 Watts, a deposition pressure is $1\times10^{-3}$ Torr, and at least one of Nitrogen (N2) and Argon (AR) flow is 10:40 sccm.

Yet another exemplary embodiment and/or exemplary method is directed to providing the fabrication of a broad spectrum waveguide structure, in which the micro-machining of the wide bandgap semiconductor thin film further includes arranging the wide bandgap semiconductor thin film on a scanning stage of an excimer laser micro-machining arrangement, and ablating the wide bandgap semiconductor thin film at selective areas with laser energy pulses to form the waveguide channels.

Still another exemplary embodiment and/or exemplary method is directed to providing a fabrication of the broad spectrum waveguide structure, in which the wide bandgap semiconductor thin film is ablated with 300 to 1500 laser energy pulses having 194.4 mJ of energy.

Yet another exemplary embodiment and/or exemplary method is directed to providing a fabrication of the broad spectrum waveguide structure, in which the wide bandgap semiconductor thin film is ablated with 1350 to 1875 laser energy pulses having 155.52 mJ of energy.

Still another exemplary embodiment and/or exemplary method is directed to providing a fabrication of the broad spectrum waveguide structure, in which the wide bandgap semiconductor thin film is ablated with 500 to 2500 laser energy pulses having 116.64 mJ of energy.

Yet another exemplary embodiment and/or exemplary method is directed to providing a fabrication of the broad spectrum waveguide structure, in which the wide bandgap semiconductor thin film is ablated with 2250 to 3750 laser energy pulses having 77.76 mJ of energy.

Still another exemplary embodiment and/or exemplary method is directed to providing a fabrication of the broad spectrum waveguide structure, in which the wide bandgap semiconductor thin film is ablated with 1500 to 7500 laser energy pulses having 194.4 mJ of energy.

Yet another exemplary embodiment and/or exemplary method is directed to providing a fabrication of the broad spectrum waveguide structure, in which the selective areas are approximately 15 microns wide and 2.5 µm deep.

Still another exemplary embodiment and/or exemplary method is directed to providing a fabrication of the broad waveguide structure, in which the laser energy pulses have a frequency of 5 Hz.

Yet another exemplary embodiment and/or exemplary method is directed to providing a fabrication of the broad spectrum waveguide structure, further including an integration of the waveguide structure into a physiological drug delivery system.

Yet another exemplary embodiment and/or exemplary method is directed to providing a fabrication of the broad spectrum waveguide structure, including an integration of the waveguide structure into a miniaturized spectrometer system.

DETAILED DESCRIPTION

Figure 1:
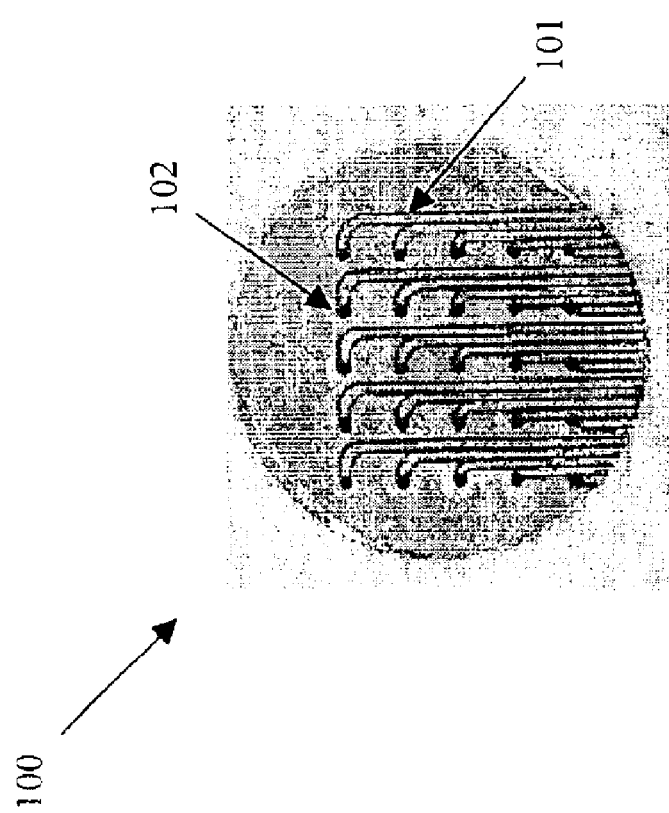
FIG. 1 shows an exemplary waveguide structure fabricated on an aluminum nitride (AlN)/sapphire substrate.

FIG. 1 shows an exemplary waveguide structure 100 fabricated on an aluminum nitride (AlN)/sapphire substrate. The dark areas (approximately 15 micron wide and 2.5 μm deep) represent areas where the aluminum nitride (AlN) wide bandgap semiconductor material has been ablated by laser energy and the light areas represent the non-ablated areas that were not exposed to the laser energy. In particular, the dark lines 102 represent the boundaries of the waveguide channels that transmit the light and the dark holes represent a pixelated array for the light to exit the waveguide structure 100. The entire waveguide structure 100 is approximately slightly less than 2 mm×2 mm.

Figure 2A:
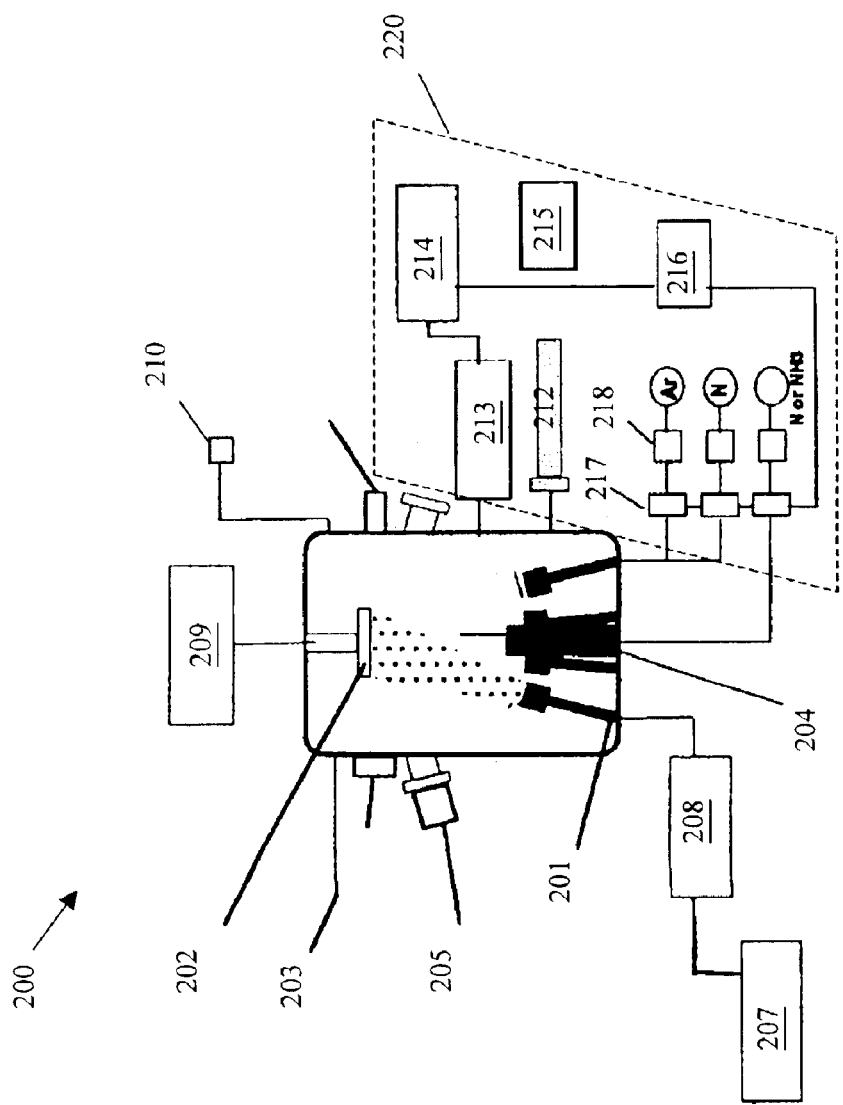
FIG. 2A shows an exemplary embodiment of a plasma source molecular beam epitaxy (PSMBE) system.

FIG. 2A shows an exemplary embodiment of a plasma source molecular beam epitaxy (PSMBE) system 200 for preparing wide bandgap materials at low temperatures, which may be used to fabricate the broad spectrum waveguide structures. The plasma source molecular beam epitaxy (PSMBE) system 200 includes a plasma source molecular beam epitaxy (PSMBE) source 201 and a rotating heated substrate holder 202 enclosed in an ultra high vacuum (UHV) chamber 203 with a high base pressure. For example, the high base pressure may be in the upper $10^{-11}$ Torr region. Wafers (which may be up to three inches for example) may be loaded on the rotating heated substrate holder 202.

The plasma source molecular beam epitaxy (PSMBE) system 200 may also include in-situ analytical systems, such as an infrared pyrometer 204 for measuring substrate temperatures, an optical spectrometer 205 for analyzing the plasma, a 35 kV reflective high-energy electron diffraction (RHEED) system 206 for analyzing film, and a spectroscopic ellipsometry system 207. Such analytical systems may operate in real-time to provide added versatility in controlling wide bandgap semiconductor film growth in the plasma source molecular beam epitaxy (PSMBE) system 200.

The plasma source molecular beam epitaxy (PSMBE) system 200 may also include a radio frequency (RF) sputtering power supply 207 with an auto-matching network 208 connected to the plasma source molecular beam epitaxy (PSMBE) source 300, a substrate bias power supply 209 (which may be fed via the rotating substrate holder 202), a capacitance manometer 210, a 30 KeV reflective high-energy electron diffraction (RHEED) gun 211, and a mass flow control system 220. As shown, the mass flow control system 220 includes a cryopump 212, a differential pumping device 213, a residual gas analyzer 214, an ion pump 215, a controller 216, and individual mass flow arrangements 217, as well as gas purifier arrangements 218 for each element (such as, for example, argon (Ar), nitrogen (N), and ammonia ($NH_3$)).

Figure 2B:
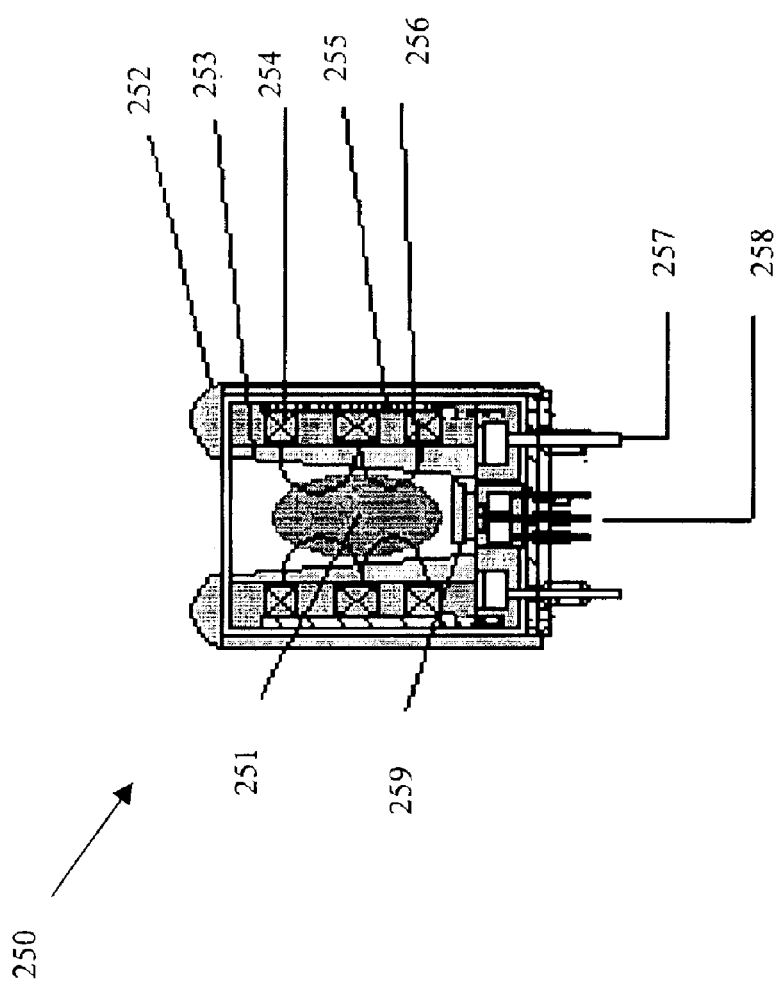
FIG. 2B shows an exemplary embodiment of a magnetically enhanced hollow cathode deposition system for growing wide bandgap semiconductors.

FIG. 2B shows an exemplary embodiment of the plasma source molecular beam epitaxy (PSMBE) source 201 of FIG. 2A implemented using a magnetically enhanced hollow cathode arrangement 250. A plasma 251 (which may be nitrogen or nitrogen/argon) is formed within the magnetically enhanced hollow cathode 250, which includes impeller 259 to provide an acceleration intake bias (negative potential) via a gas inlet 258. The walls 252 of the magnetically enhanced hollow cathode 250 are lined with a target deposition material 253. This target deposition material 253 may be 99.99999% pure molecular beam epitaxy (MBE) grade aluminum (Al) or another suitably appropriate deposition material. Magnets 254 and magnetic return 255 are provided to induce a magnetic field 256. A radio frequency (RF) or pulsed dc power 257 is coupled to the magnetically enhanced hollow cathode 250, which is intended to provide an efficient plasma formation due to the hollow cathode effect and the magnetically induced effective pressure increase.

During operation, the plasma 251 dissociates the diatomic nitrogen molecule into radical ions, as well as other combinations. The ions sputter atoms from a surface of the magnetically enhanced hollow cathode 250 (such as, for example, in a normal direction). Multiple collisions may occur before an aluminum (Al) atom or ion escapes as the nitrogen and aluminum ions are accelerated to an appropriate specific energy. The specific energy for aluminum nitride (AlN) is believed to be 12 eV. The atoms condensing onto the substrate (i.e. adatoms) may therefore have highly regulated energy. Thus, crystal growth may occur even at low substrate temperatures (such as for example, below 400° C.). Furthermore, the aluminum nitride (AlN) crystal growth may be tailored from a polycrystalline structure to a near single-crystalline structure, which may include both hexagonal and other-shaped structures. For example, a single high quality crystal formed using aluminum nitride (AlN) may be grown on a sapphire-based substrate. It is believed that silicon and sapphire substrates may have considerable lattice mismatch, so that even epitaxial growth may be strained. It is believed that, however, using a compliant amorphous aluminum nitride (AlN) layer may provide nearly stain-free aluminum nitride (AlN) growth. The aluminum nitride (AlN) films grown on sapphire substrates may be removed to form free standing crystals by irradiating through the sapphire wafer using high energy Excimer laser pulses. The resulting films may then be micro-machined into free standing bridge structures.

Using the magnetically enhanced hollow cathode arrangement 200, the plasma source molecular beam epitaxy (PSMBE) source 201 may be configured to permit wide-ranging parameter control, including parameters such as the flux energy (that is, the energy ranging from thermal to high energy due to an added bias) of the depositing species achieving precise composition control. In addition, samples may be immersed directly into the hollow cathode plasma for complete 360-degree encapsulation with the wide bandgap semiconductor. Thus, for example, a miniaturized Si-based microelectronic device or chip may be completely encapsulated in wide bandgap semiconductors which may be post-processed into functionally active device structures directly integrated into the microelectronic chip.

Figure 2C:
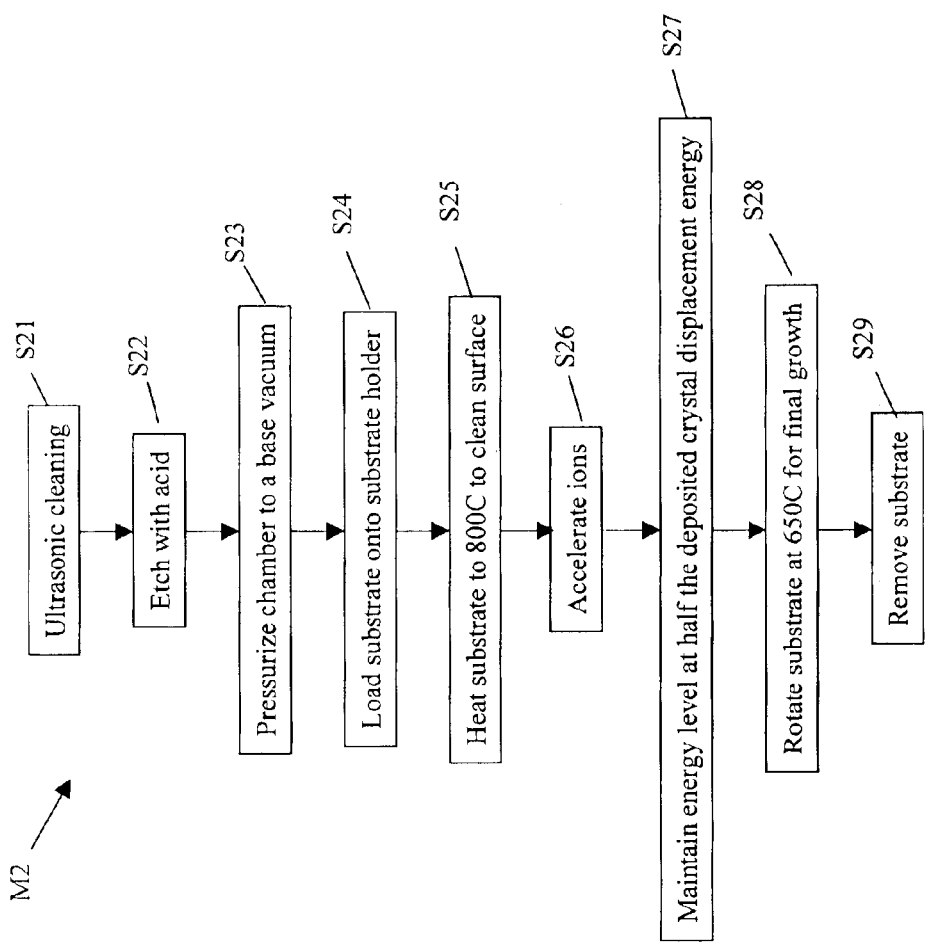
FIG. 2C shows an exemplary method for depositing a aluminum nitride (AlN) wide bandgap thin film onto a sapphire substrate.

FIG. 2C shows an exemplary method M2 for depositing a wide bandgap material, such as, for example, aluminum nitride (AlN), onto a substrate, such as, for example a C-plane double side epi-polished [0001] sapphire substrate. In step S21, the sapphire substrate is ultrasonically cleaned using, for example, acetone and methanol. In step S22, the substrate is etched in acid, such as, for example, a 3:1 mixture of sulfuric acid and phosphoric acid. In step S23, the ultra high vacuum (UVH) chamber 203 of the plasma source molecular beam epitaxy (PSMBE) system 200 is pumped to a base vacuum pressure of $1 \times 10^{-10}$ Torr. In step S24, the sapphire substrate is loaded onto the substrate holder 202. In step S25, the substrate is heated to a high temperature, such as, for example, 800° C., to perform a final cleaning of the surface of the substrate. In step S26, the impeller 259 of the plasma molecular beam epitaxy (PSMBE) source 201 is operated to provide ion acceleration. In step S27, an energy level of approximately half that of deposited crystal displacement energy is maintained to ensure maximum mobility, proper bond formation, ejection of contaminants, and quality crystal growth while eliminating, or at least minimizing ion induced damage to the growing crystal. The aluminum (Al) source is kept at 200 Watts and the Nitrogen (N2) and Argon (AR) flow is kept at 10:40 sccm. The dynamic radio frequency power is maintained at $1 \times 10^{-3}$ Torr during deposition, and the temperature is maintained at, for example, 650° C., or 400° C. if a buffer layer is required. In step S28, the substrate is rotated into the deposition line of sight at approximately 650° C. for final growth of the aluminum nitride (AlN) wide bandgap material. The resulting grown material may form a thin film in the range of, for example, 0.2 to 2 μm in thickness, or thicker if desired.

Table 1 outlines deposition parameters for growth of the aluminum nitride (AlN) wide bandgap thin film on the sapphire substrate.

TABLE 1

Outline of the deposition parameters for growth of AlN films deposited on a sapphire substrate

| Substrate Temperature(Co) | Source Power (r.f. Watts) | Bias Voltage (−V) | Base Pressure (Torr) | Deposition Pressure (Torr) | Nitrogen Flow (SCCM) |
|---|---|---|---|---|---|
| 650 | 200 | 12 | 1 × 10E−10 | 1 × 10E−3 | 10 |

Figure 3A:
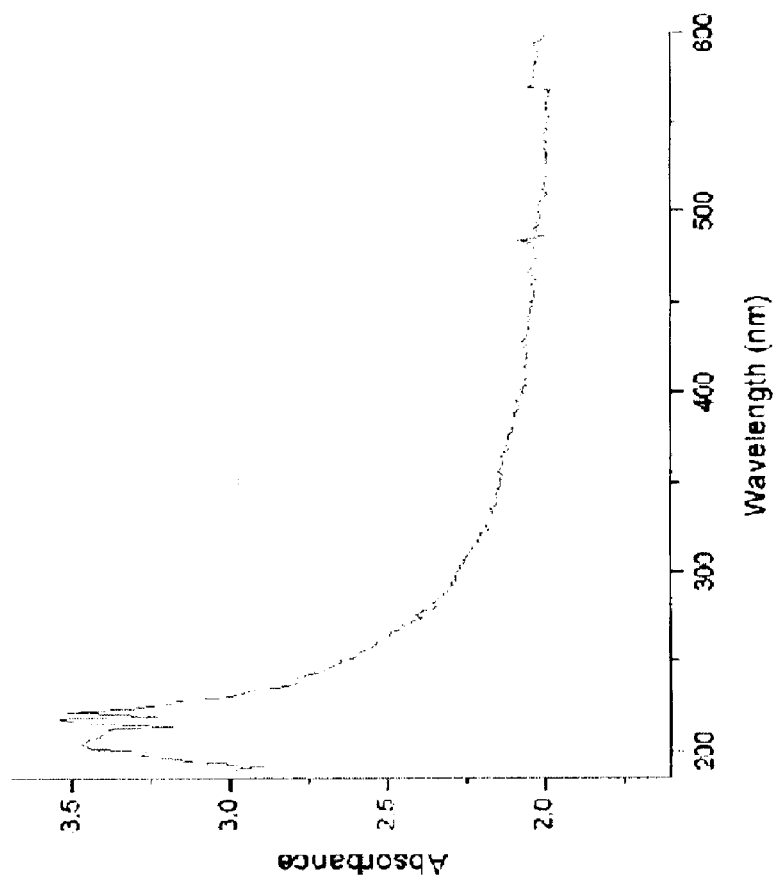
FIG. 3A shows spectroscopic data for an aluminum nitride (AlN) thin film.

FIG. 3A shows spectroscopic data for an aluminum nitride (AlN) thin film. The optical transmittance from the aluminum nitride (AlN) thin film deposited on the sapphire substrate shows that the absorption edge of the thin film is approximately 200 nm, which corresponds to a bandgap energy of approximately 6.2 eV. As measured by the spectroscopic ellipsometry system 205, the aluminum nitride (AlN) thin film and sapphire substrate have indexes of refraction of n=2.1 and n=1.6 respectively, so that the maximum absorption of the aluminum nitride (AlN) appears to be in the very deep ultraviolet (UV) range. Hence, the aluminum nitride (AlN) thin films deposited on sapphire substrates may be a suitable candidate for broad spectrum waveguides that operate in the deep ultraviolet (UV) range.

Figure 3B:
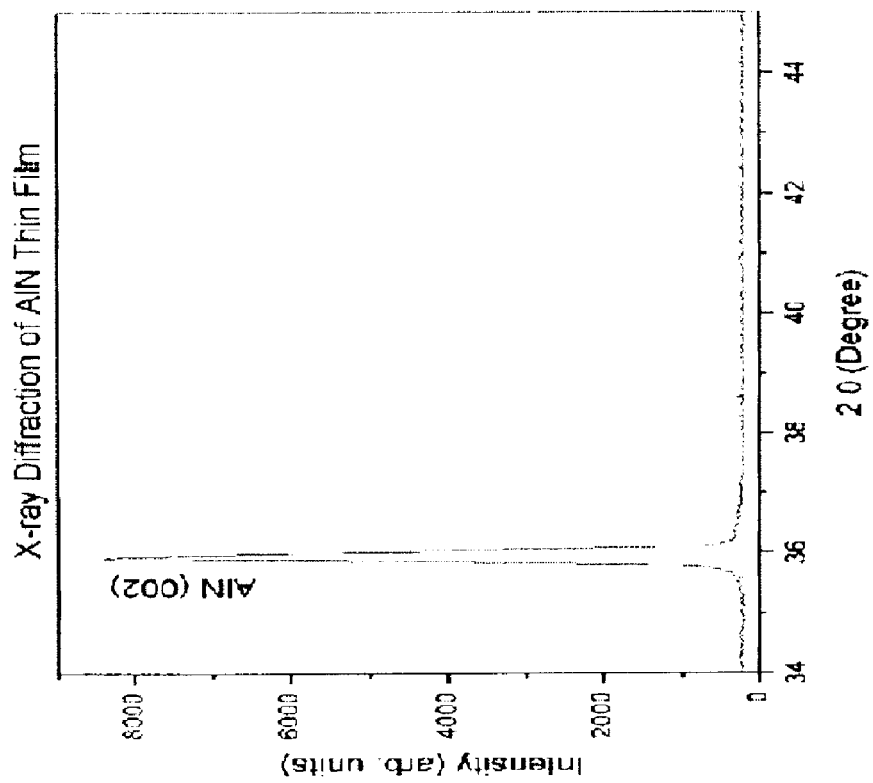
FIG. 3B shows an X-ray diffraction analysis of an aluminum nitride (AlN) thin film.

FIG. 3B shows an X-ray diffraction analysis of an aluminum nitride (AlN) thin film. As shown, the aluminum nitride (AlN) thin film is highly C-axis oriented so that the thin film has minimal grain boundaries and is not polycrystalline.

Figure 3C:
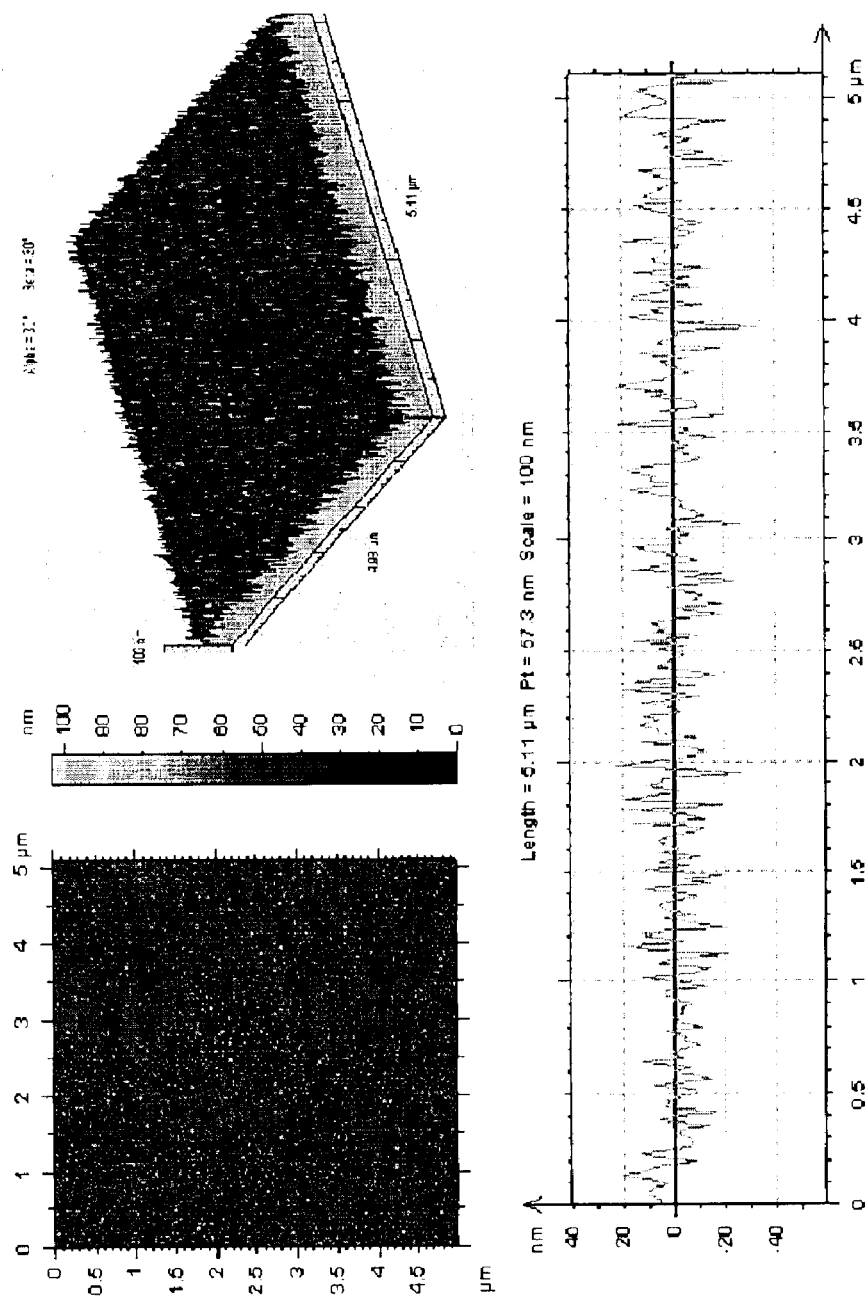
FIG. 3C shows an Atomic Force Microscopy and Profile of film roughness for the aluminum nitride (AlN) thin film.

FIG. 3C shows an Atomic Force Microscopy and Profile of film roughness of the deposited aluminum nitride (AlN) thin film. Through the use of Atomic Force Microscopy, the surface topology of the aluminum nitride thin film may be observed. According to FIG. 3C, the deposited thin film is atomically smooth with a root-mean-square roughness of approximately 2 nm. It is believed that these results indicate that deposition by the plasma source beam epitaxy (PSMBE) system 200 should provide epitaxial-growth surfaces that are suitable for an efficient waveguiding system. In particular, it is believed that this smoother surface may provide a better optical waveguide.

The exemplary embodiments and/or exemplary methods of the present invention may involve the use of Excimer laser technology to micro-machine wide bandgap thin films into arrays of submicron waveguide structures. Excimer lasers operate in the ultra-violet (UV) range thereby emitting high photon energy (Excimer stands for "excited dimmer", a diatomic molecule, which may be an inert gas atom and a halide atom (having a very short lifetime) and which dissociate releasing energy through ultra-violet (UV) photons).

Figure 4A:
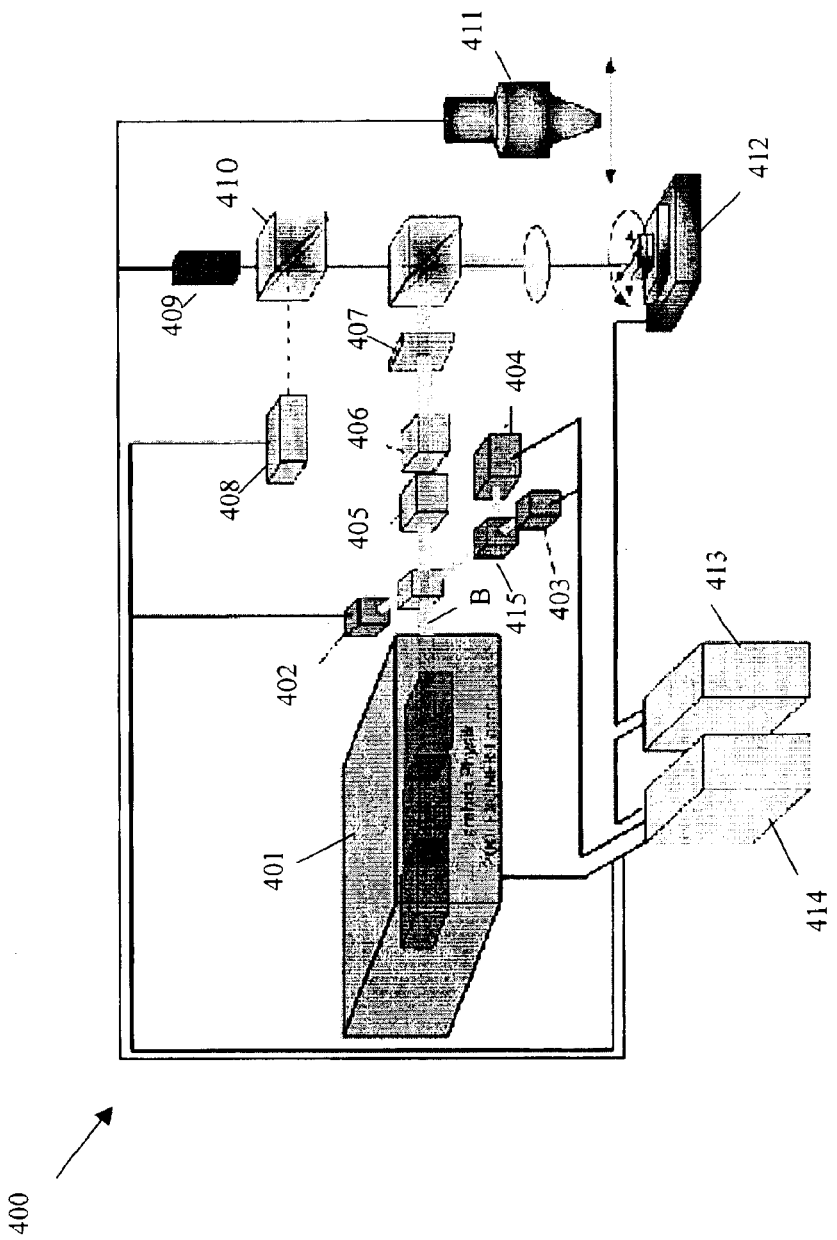
FIG. 4A shows an exemplary embodiment of an Excimer laser micro-machining arrangement to fabricate waveguide structures.
Figure 4B:
FIG. 4B shows an operational example of the Excimer laser micro-machining arrangement of FIG. 4A.
Figure 4C:
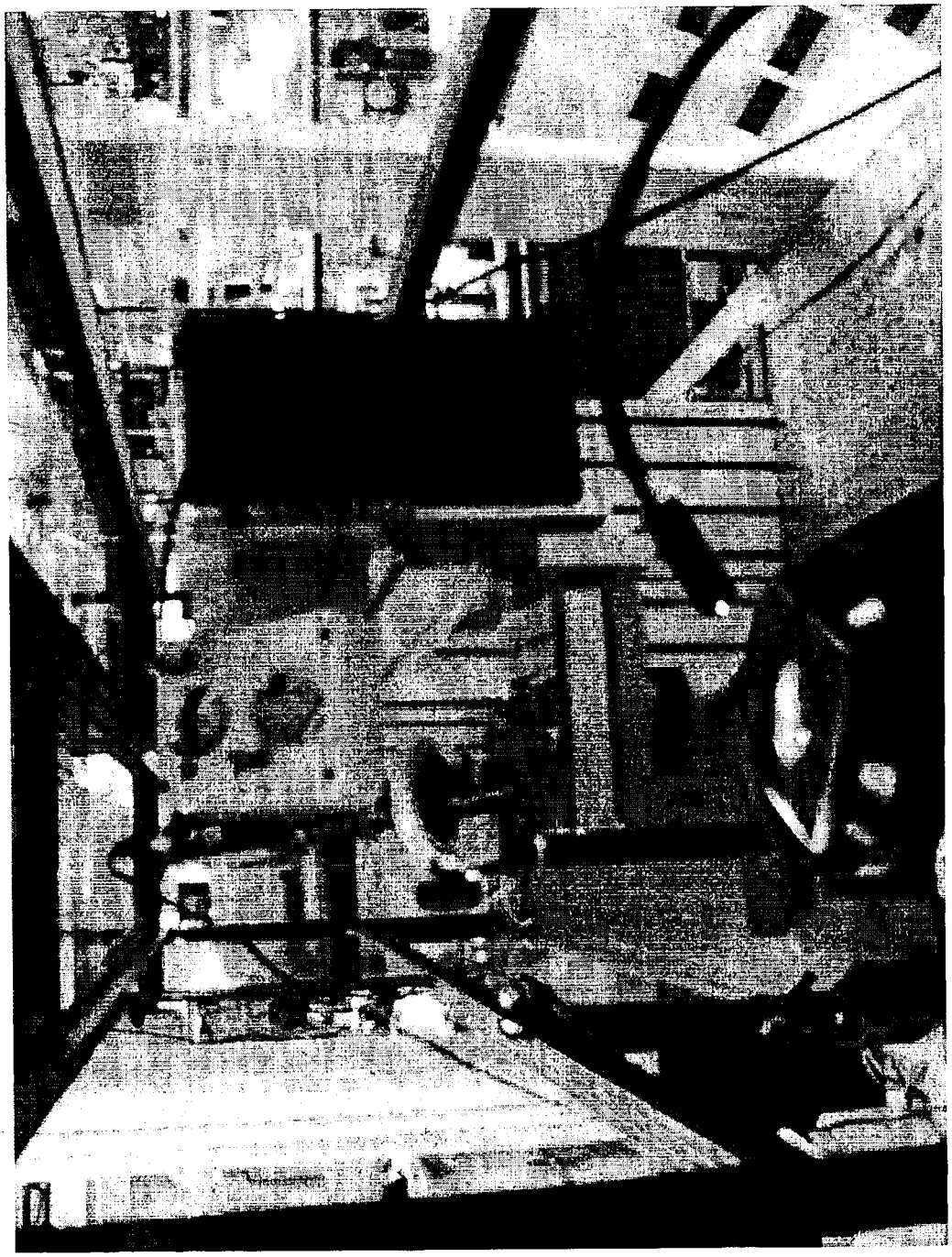
FIG. 4C shows an alternative view of the exemplary operational Excimer laser micro-machining arrangement of FIG. 4B.

FIG. 4A shows an exemplary embodiment of an Excimer laser micro-machining arrangement 400 to micro-machine waveguide structures. As shown, the Excimer laser micro-machining arrangement 400 includes a laser source 401 (such as, for example, a Lambda Physik 200 Excimer laser), which may be capable of submicron step and repeat, or a mask may be used to for high speed fabrication. The Excimer laser micro-machining arrangement 400 may be operated in a KrF mode so as to emit a wavelength of about 248 nanometers, for example. Operating at this wavelength is intended to provide superior results when compared to operation at smaller emitted wavelengths. The resulting laser beam B may reach an energy level on the order of about 600 milli-Joules, for example, with a pulse duration of 25 nanoseconds and a rectangular output beam having dimensions of about 23 mm×8 mm. The laser beam B passes through a neutralized continuously tunable attenuator arrangement 405 and a homogenizer arrangement 406 having a micro-lens array arrangement. The micro-lens array arrangement of the homogenizer 406 is used to split the laser beam B into different beamlets traveling along different paths, and may also be used to overlap them on a plane to be irradiated, which is associated with the mask 407.

The mask 407 is placed in the homogenized plane (with a homogenized illumination area of 18 mm×18 mm, for example) and imaged by an objective lens onto the sample with, for example, a ten-fold (10×) reduction. The sample may be placed on top of an ultra-precision 4-dimensional scanning stage 412 (which may be, for example, a Newport PM500, X, Y, Z and rotation; X and Y with 80 mm travel limit, and 0.05 μm-linear resolution; Z with 25 mm travel limit, and 0.025 μm linear resolution; rotation stage with 360° travel, and 0.00030 rotary resolution). A photon beam profiler 404 may be used to measure the laser beam intensity profile, and a pyroelectric energy sensor 402 is used to measure the laser pulse energy and a fast-response. A photodiode 415 (such as, for example, a Hamamatsu photodiode) is used to measure the pulse time shape. A processor arrangement 414 and motion control system 413 may be used to control the Excimer laser micro-machining arrangement 400. This may include control of the laser source 401, sample scanning stage to control micropatterning design and fabrication, and laser beam characterization. The Excimer laser micro-machining arrangement 400 may also include a computer controlled display (CCD) camera 408, an alignment laser arrangement 409, a beam splitter 410, and an optical surface profiler (interferometer) 411.

According to one exemplary method of operating the Excimer laser micro-machining arrangement 400, a 2 μm aluminum nitride (AlN) thin film (grown, for example, on a sapphire substrate by the plasma source beam epitaxy (PSMBE) system 200) may be secured to the ultra-precision 4-dimensional scanning stage 412 and ablated with, for example, five (5) equally spaced laser energy pulses at 5 Hz frequency. The laser energy pulses may be controlled by the processor arrangement 414 and motion control system 413 according to the exemplary parameters outlined in Table 2 below.

TABLE 2

Excimer Laser Ablation Parameters

| Trial# | Energy (mJ) | Pulse # |
|---|---|---|
| 1.1 | 194.4 | 1500 |
| 1.2 | 194.4 | 1200 |
| 1.3 | 194.4 | 900 |
| 1.4 | 194.4 | 600 |
| 1.5 | 194.4 | 300 |
| 2.1 | 155.52 | 1875 |
| 2.2 | 155.52 | 1500 |
| 2.3 | 155.52 | 1350 |
| 2.4 | 155.52 | 900 |
| 2.5 | 155.52 | 450 |
| 3.1 | 116.64 | 2500 |
| 3.2 | 116.64 | 2000 |
| 3.3 | 116.64 | 1500 |
| 3.4 | 116.64 | 1000 |
| 3.5 | 116.64 | 500 |
| 4.1 | 77.76 | 3750 |
| 4.2 | 77.76 | 3000 |
| 4.3 | 77.76 | 2250 |
| 4.4 | 77.76 | 1500 |
| 4.5 | 77.76 | 750 |
| 5.1 | 38.88 | 7500 |
| 5.2 | 38.88 | 6000 |
| 5.3 | 38.88 | 4500 |
| 5.4 | 38.88 | 3000 |
| 5.5 | 38.88 | 1500 |

Figure 5A:
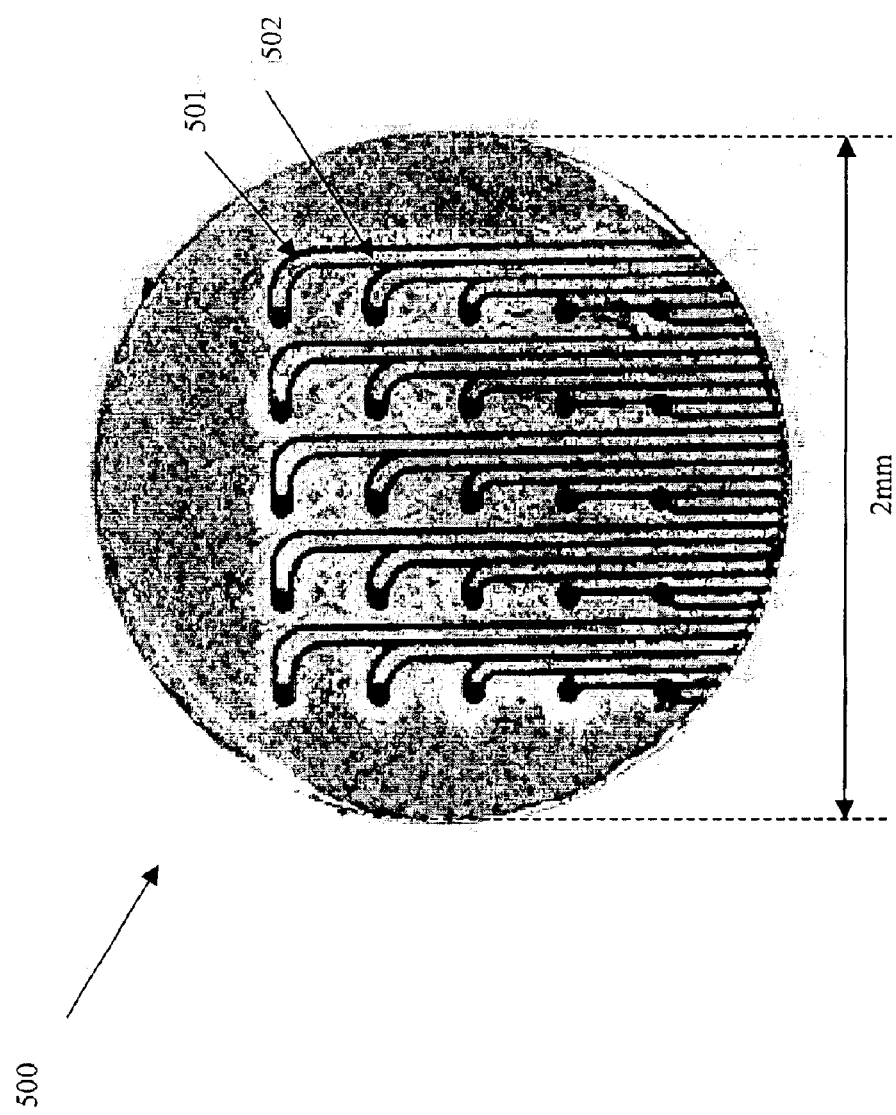
FIG. 5A shows a micro-machined waveguide structure.

FIG. 5A shows a micro-machined waveguide structure 500 that was fabricated using the Excimer laser micro-machining arrangement 400 with five hundred (500) pulses at 116.64 mJ of energy at 5 Hz frequency. The dark areas 501, which are approximately 15 microns wide, represent the micro-machined areas where the 2 μm aluminum nitride (AlN) thin film has been ablated by the Excimer laser energy pulses. The brighter areas 502 represent non-ablated areas of the 2 μm aluminum nitride (AlN) thin film that were not exposed to the Excimer laser energy pulses. The combination of the ablated dark areas 501 and non-ablated brighter areas 502 forms a "trench" or channel that may propagate light within, for example, the ultraviolet range (UV), due to the difference in index of refraction properties between the dark and light areas. In the example, the dark areas have an index of refraction of 1.6 and the light areas have an index of refraction of 2.1.

The waveguide structure 500 of FIG. 9A includes 25 waveguide channels, each channel having a width of approximately 50 μm for an overall width of approximately slightly less than 2 mm (that is, the light areas between the ablated dark lines are approximately 50 μm wide and the dark lines themselves are each approximately 5 μm wide). Such a configuration or arrangement of the waveguide channels is believed to maximize the intensity of ultraviolet (UV) light propagating therein. Other configurations may be provided depending on the spectrum of light desired to be transmitted.

Figure 5B:
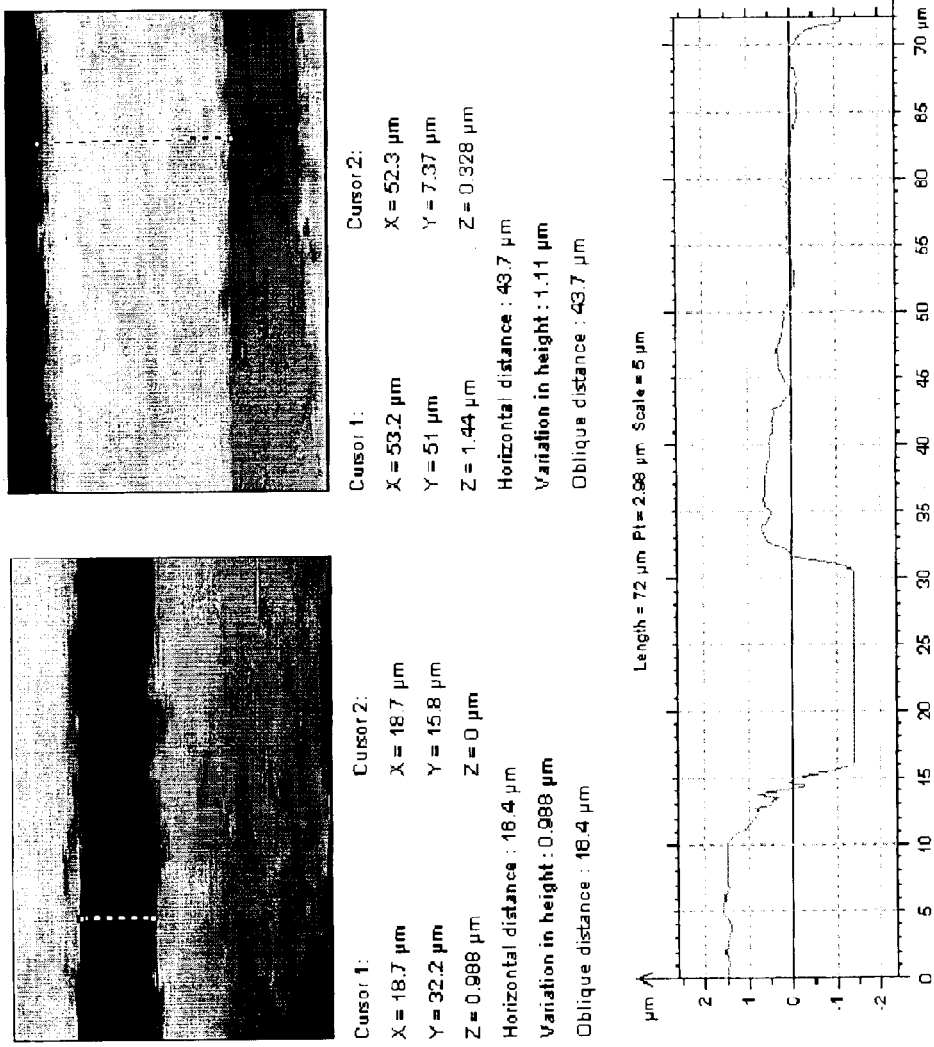
FIG. 5B shows an Atomic Force Microscopy and Profile of a waveguide channel of the waveguide structure of FIG. 5A.

FIG. 5B shows an Atomic Force Microscopy and Profile of a micro-machined waveguide channel of FIG. 5A.

Figure 5C:
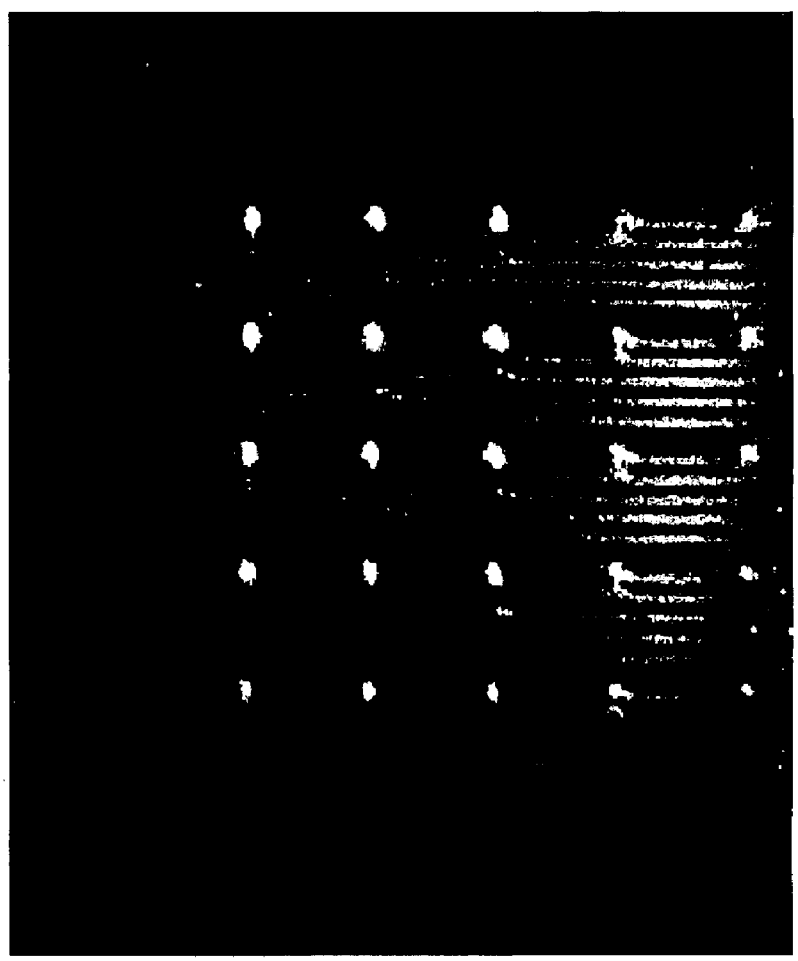
FIG. 5C shows a light pattern produced when a light emitting diode is coupled to the waveguide structure of FIG. 5A.

FIG. 5C shows a light pattern produced when a 3.9V light emitting diode (LED) is coupled to the waveguide structure 501 of FIG. 5A. The illuminated areas demonstrate the propagation of light within channels of the waveguide structure 501 and its subsequent release through the pixelated array openings. To minimize the leakage of light, the waveguide channels may be provided with a coating, such as, for example, titanium.

Figure 5D:
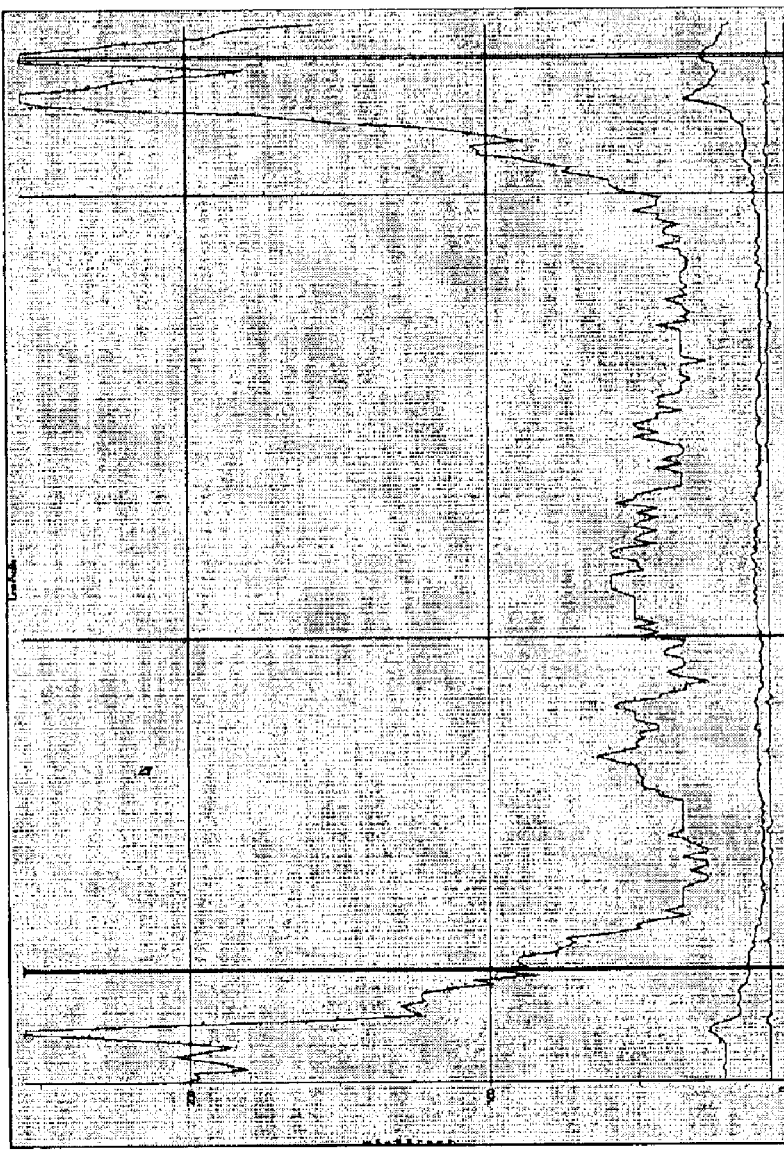
FIG. 5D shows luminescence through two pixels of the light emitted from the waveguide structure of FIG. 5A.

FIG. 5D shows luminescence through two pixels of the light emitted from the waveguide structure of FIG. 5A, as measured by an Optronics Magnafire camera and associated software.

Figure 6A:
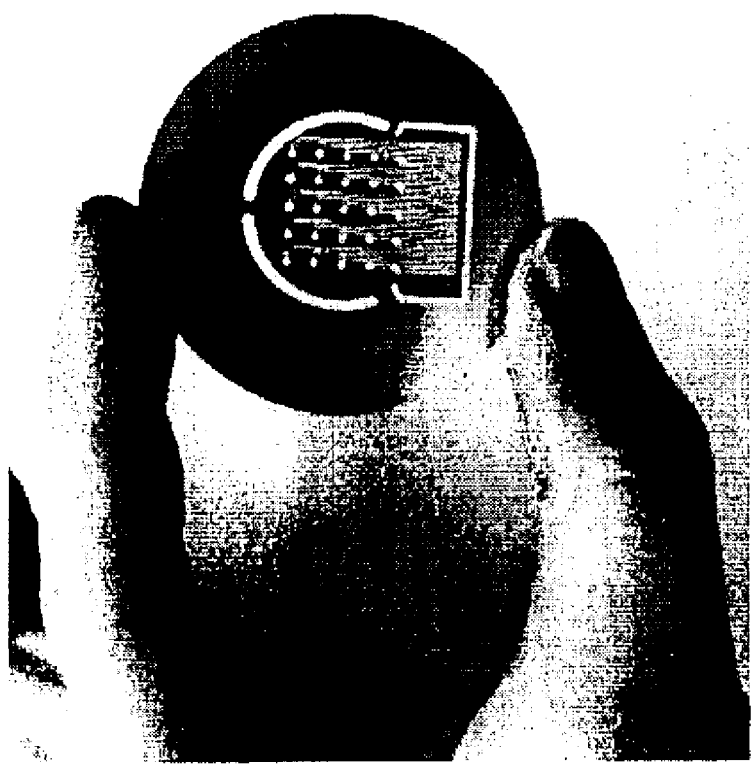
FIG. 6A shows an exemplary stainless steel patterned stencil that may be used to define the geometry of the micro-machined waveguide structure of FIG. 5A.

FIG. 6A shows an exemplary stainless steel patterned stencil that may be used to define the geometry of the micro-machined waveguide structure 501 of FIG. 5A.

Figure 6B:
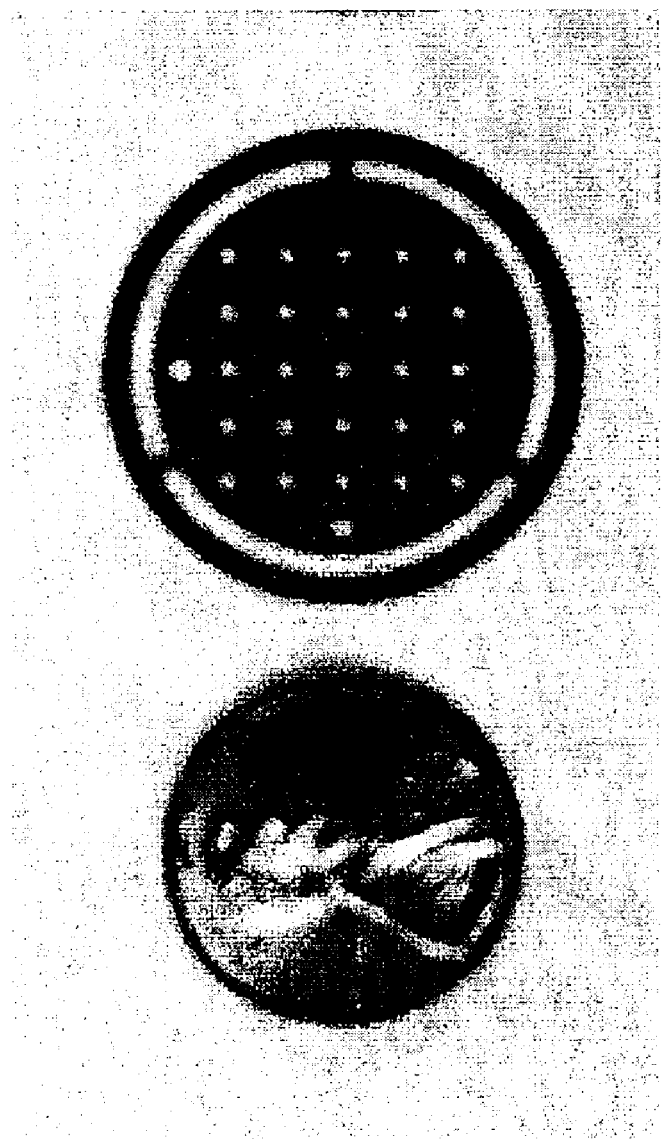
FIG. 6B shows an exemplary stainless steel patterned stencil that may be used to define the geometry of a complementary pixelated array interface for the micro-machined waveguide structure of FIG. 5A, and its comparative size.

FIG. 6B shows an exemplary stainless steel patterned stencil that may be used to define the geometry of a complementary pixelated array interface for the micro-machined waveguide structure of FIG. 5A, and its comparative size.

Figure 6C:
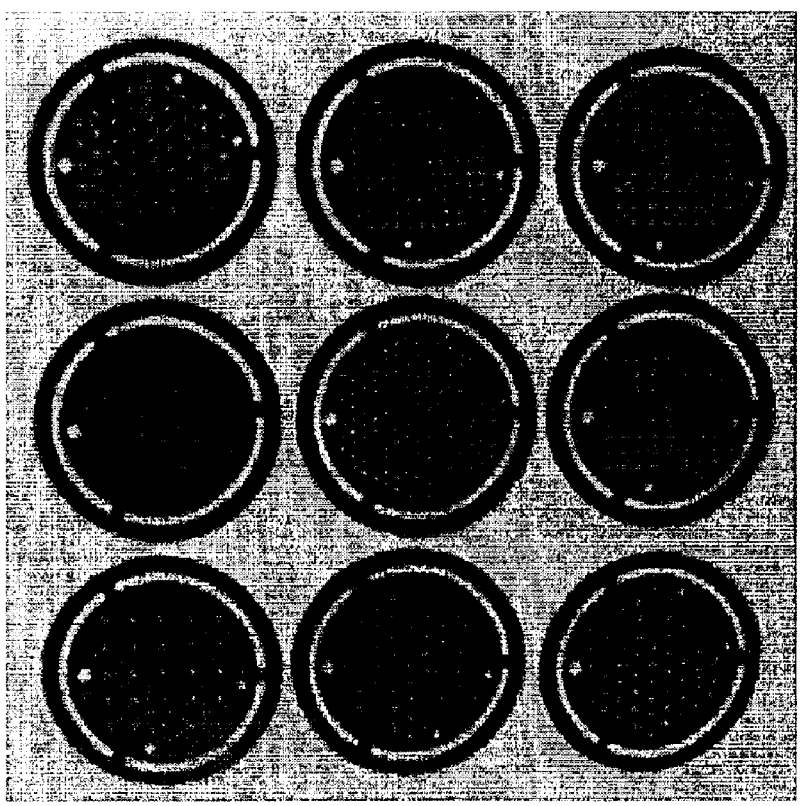
FIG. 6C shows further exemplary stainless steel patterned stencils.

FIG. 6C shows further exemplary stainless steel patterned stencils having a variety of patterns. Each stainless steel patterned stencil or mask may constructed larger (for example, 10 times larger) than the intended interface (with up to, for example, 184 pixels).

Figure 7:
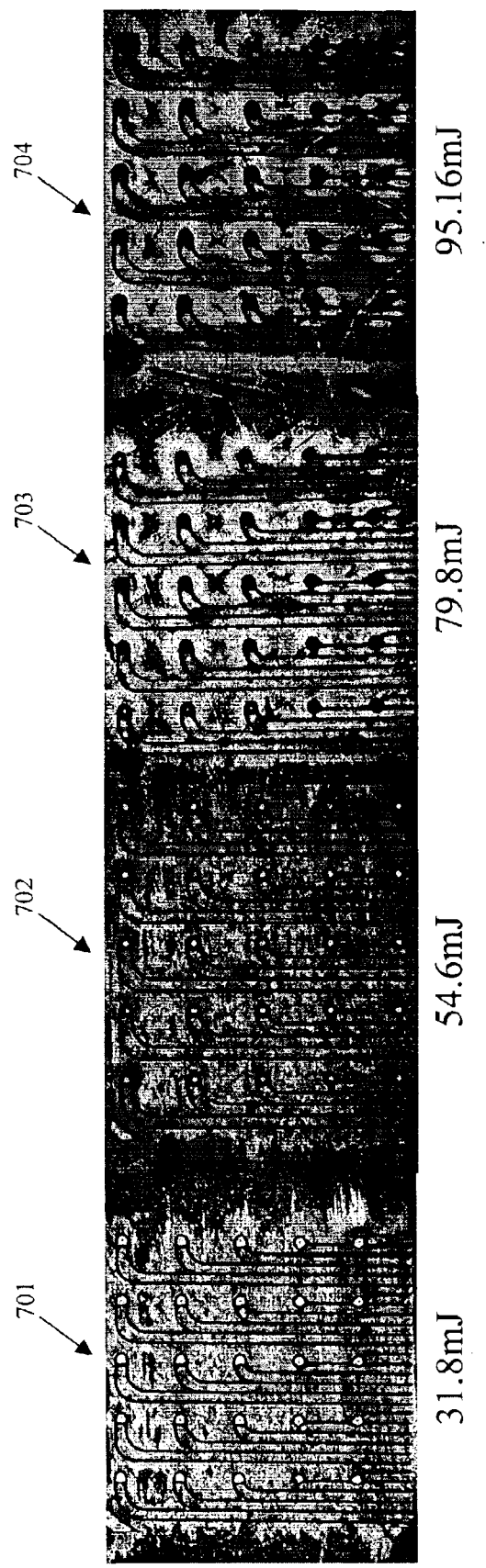
FIG. 7 shows exemplary waveguide structures ablated with various levels of pulse energy.

FIG. 7 shows exemplary waveguide structures micromachined from a 2.1 micron thin layer of aluminum nitride (AlN) deposited on a sapphire substrate, each waveguide structure being ablated for six minutes with a different level of energy from a 5 Hz laser pulse. In particular, FIG. 7 shows a first waveguide structure 701 ablated with 31.8 mJ of energy, a second waveguide structure 702 ablated with 54.6 mJ of energy, a third waveguide structure ablated with 79.8 mJ of energy, and a fourth waveguide structure 704 ablated with 95.16 mJ of energy.

Figure 8:
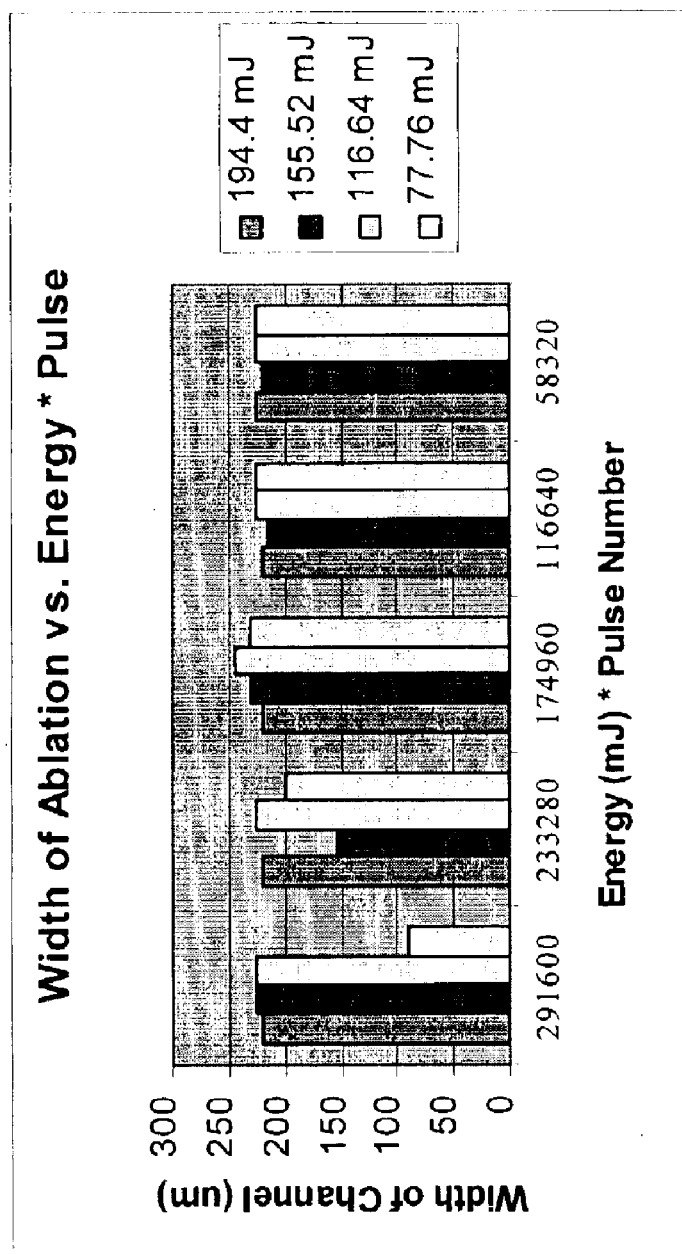
FIG. 8 shows a characteristic analysis of the ablation or channel width of a waveguide structure.

FIG. 8 shows a characteristic analysis of ablation or channel width of a waveguide structure using a confocal microscopy and a Dektak 3030 profilometer. In particular, the width of the waveguide channel (ablation) is plotted versus the product of the laser energy and pulse number. As shown in FIG. 8, a channel width of approximately 225 μm may be achieved. Although deviations from this width may have been experienced at pulse-energy values of, for example, 77.76 mJ and at 155.52 mJ, such deviations may result from inconsistent profile settings of the laser beam, so deeper and more narrow channels may result. Obtaining a three-dimensional profile of the laser beam before ablation may provide more uniform laser projection at all energy levels.

Figure 9:
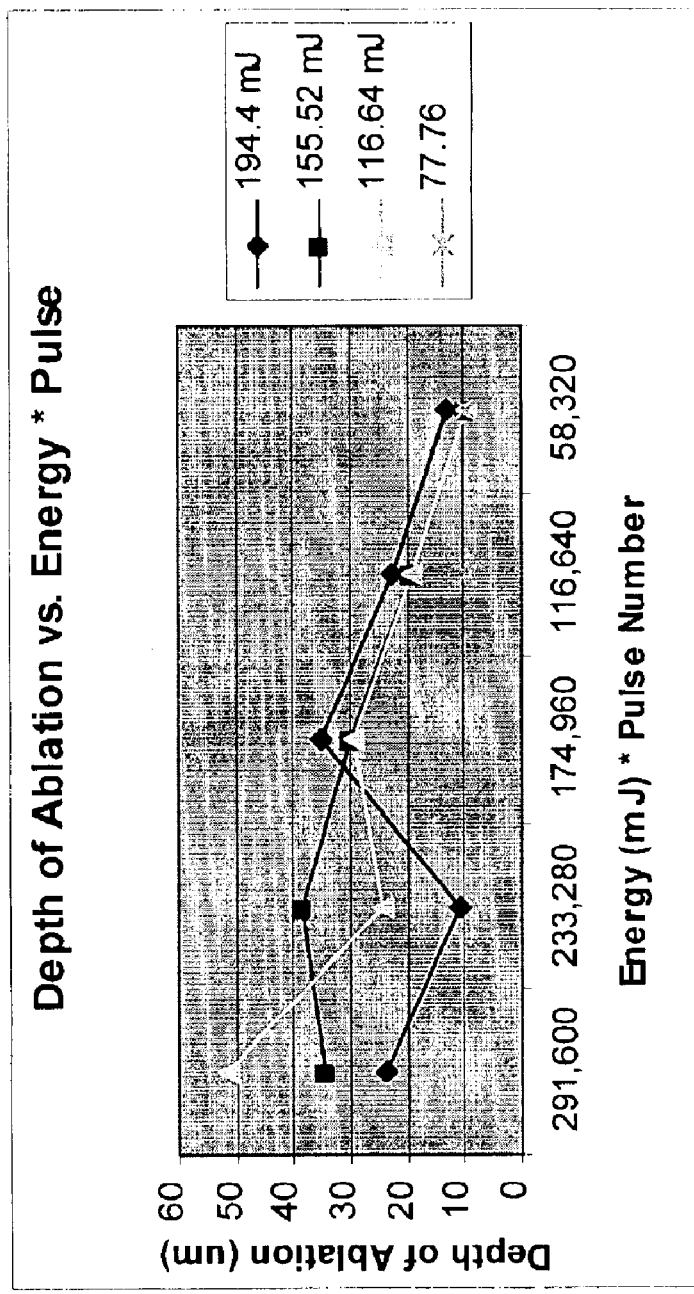
FIG. 9 shows a characteristic analysis of the ablation or channel depth of a waveguide structure.

FIG. 9 shows a characteristic analysis of the ablation or channel depth of a waveguide structure. In particular, the depth of the waveguide channel (ablation) is plotted versus the product of the laser energy and pulse number. As shown in FIG. 9, an essentially consistent ablation rate may be achieved at 194.4 mJ of energy. However, the second value of this trial indicates a deeper ablation. At 155.52 mJ of energy, a similar ablation depth pattern may be achieved except a deeper ablation may be achieved at the third measurement rather that the second. At 116.64 mJ of energy, an ablation rate pattern similar to that achieved at 194.4 mJ of energy may be achieved. At 77.76 mJ of energy, a minimal ablation depth may be achieved as compared to the other plotted measurements. Also at 77.76 mJ of energy, a metallized layer (aluminum) is observed indicating that the laser energy pulses may ablate through the aluminum nitride (AlN) and into the sapphire substrate. This may contradict the belief that sapphire may not be micro-machined by a 248 nanometer pulse since it is understood that laser ablation is initiated by photon absorption and sapphire only transmits light from 150 nm up to 8 μm. However, it is believed that a metallization catalyst may be formed to allow ablation into the sapphire substrate. Although sapphire ablation may not have been previously observed, the metallization of aluminum nitride (AlN) may act as an absorption layer providing a localized melt of the sapphire material.

Ablation results may vary at higher energies and pulse numbers due to secondary effects at the aluminum nitride (AlN)/sapphire interface at higher photon intensities. Based on this and the unobserved ablation at the lowest energy value of Table 2, the threshold value for ablation is believed to be approximately 70 mJ of energy.

According to one exemplary embodiment of the present invention, the waveguide structures may be used in a combined optical waveguide structure with a microfluidic delivery system. For a description of a microfluidic delivery system see co-pending U.S. Patent Application Ser. No. 60/212,214, entitled "Method and Apparatus for Stimulating Neurological Tissue", filed Jun. 16, 2000, the disclosure of which is incorporated by reference in its entirety herein, and corresponding PCT Application No. WO 01/97899, filed on Jun. 15, 2001 and published on Dec. 27, 2001, which is also incorporated by reference in its entirety herein. In this exemplary system, a visual prosthesis device may be provided that utilizes "caged" neurotransmitter substances to stimulate retinal and cortical tissue. Caged compounds are drug-precursors that have been inactivated due to their binding configuration to another inert molecule. It is understood, that this class of molecules requires some form of energy to cleave the inactivating cage away from the drug's biologically active site. By exposing them to brief pulses of 360-nanometer light, the cage portion of the compound may be cleaved from the physiologic active moiety on the neurostimulatory molecule. This photo-activation may occur within microseconds. Thus, it is believed that caged neurotransmitter substances (such as glutamate, glycine, and aspartate) allow the focal stimulation of neural tissue, with the specificity associated with neurotransmitters, for use as a sophisticated drug-delivery neurotransmitter-based inter-neuronal communication. It is believed that this may be achieved with a thin-film-based waveguide capable of deep ultraviolet light transmission for activating the caged neurotransmitters, as described herein.

It is believed that the exemplary combined waveguide and drug-delivery system may be applied to movement disorders such as paralysis, epilepsy, and Parkinson's disease, psychiatric diseases such as chronic depression or schizophrenia, and multiple forms of dementia, such as Alzheimer's disease, in which drug delivery systems need to breech the blood brain barrier.

Figure 10A:
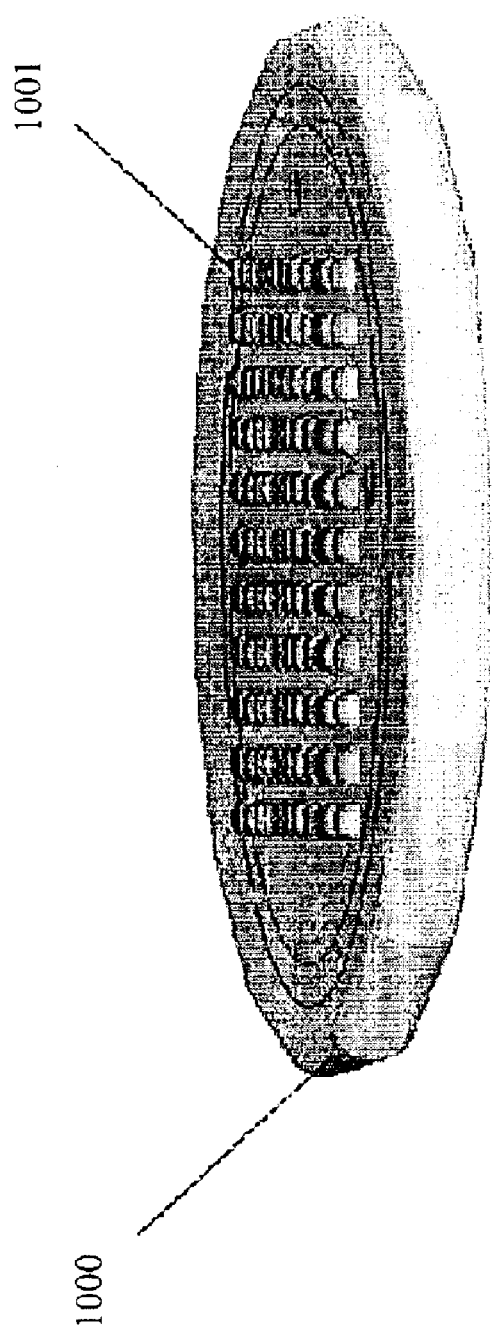
FIG. 10A shows an electro-optical microfluidic (EOM) chip arrangement with microfluidic channels for providing combined electrical and chemical stimulation.

FIG. 10 shows an electro-optical microfluidic (EOM) chip arrangement 1000 with microfluidic channels 1001 for providing combined electrical and chemical stimulation. The electro-optical microfluidic (EOM) chip arrangement 1000 may include 80 micro-diameter fluid holes and 60 micro-diameter microelectrode holes.

Figure 10B:
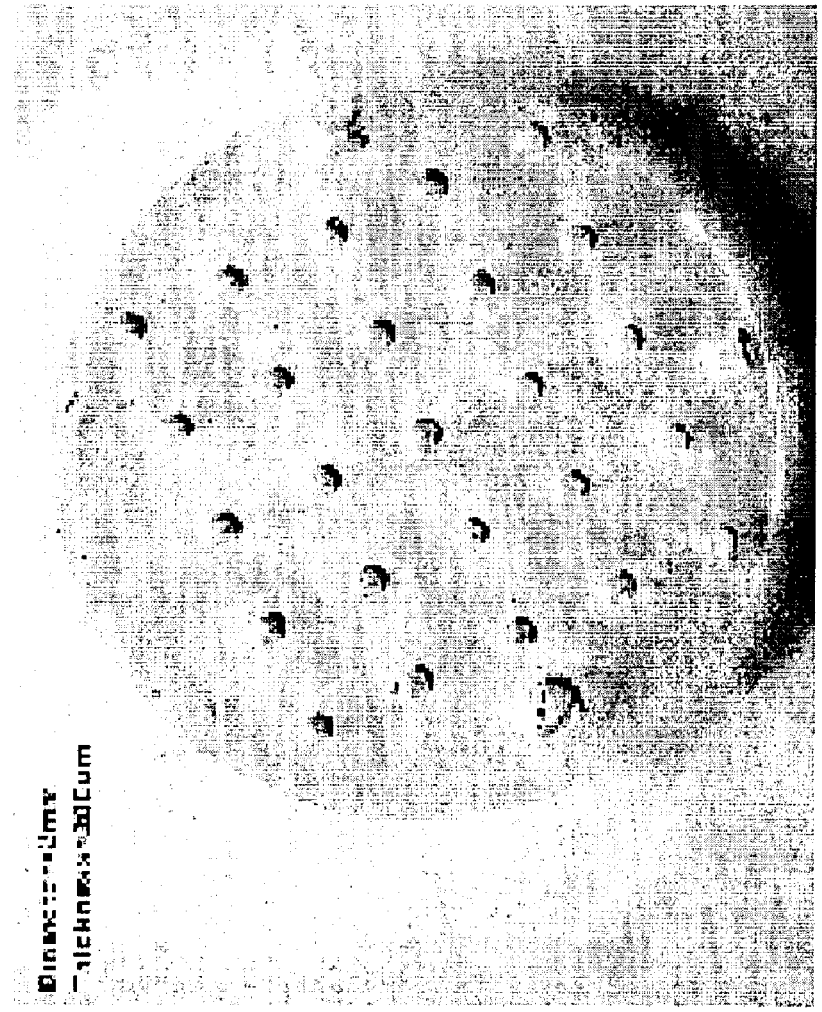
FIG. 10B shows a top down view of an electro-optical microfluidic (EOM) chip arrangement.

FIG. 10B shows a top-down view of an electro-optical microfluidic (EOM) chip arrangement.

Figure 10C:
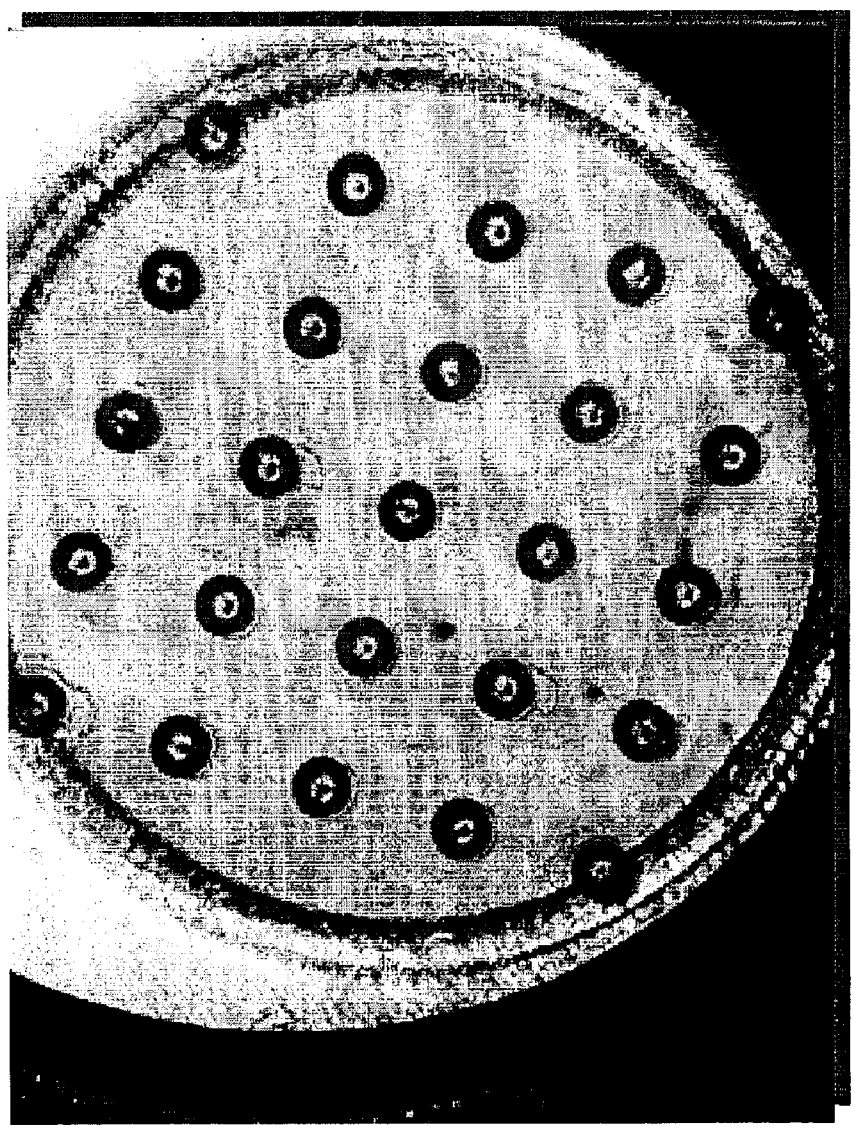
FIG. 10C shows another top down view of an electro-optical microfluidic (EOM) chip arrangement.

FIG. 10C shows another top-down view of an electro-optical microfluidic (EOM) chip arrangement.

Figure 11:
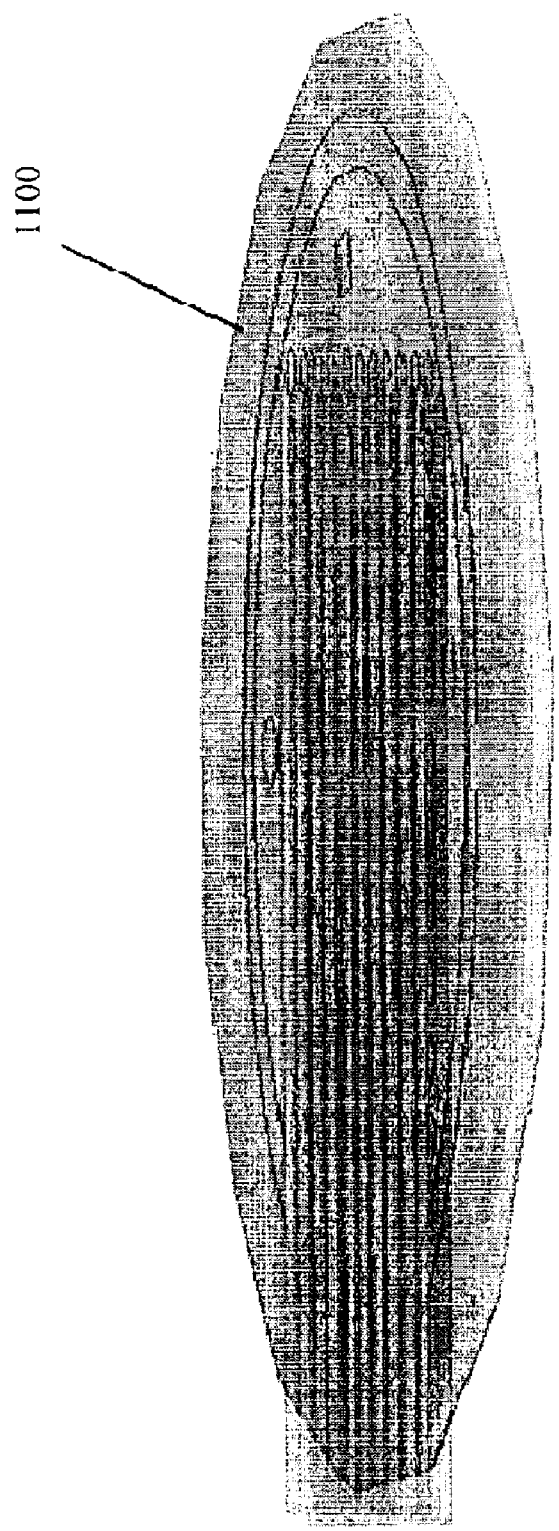
FIG. 11 shows a double sided $AlN/Al_2O_3$ waveguide structure for interfacing with the electro-optical microfluidic (EOM) chip arrangement of FIG. 10.

FIG. 11 shows a double sided AlN/Al$_2$O$_3$ waveguide structure 1100 for interfacing with the electro-optical microfluidic (EOM) chip arrangement 1000 of FIG. 10 to provide controlled spatial distribution of light. A 50 micron wide core fused silica fiber optics may be coupled to the double sided AlN/Al$_2$O$_3$ waveguide structure 1100 to deliver ultraviolet light (UV) to the waveguide structure 1100, which may then propagate the light via its waveguide channels and emit the light in a pixelated array pattern onto the microfluidic channels 1001 of the electro-optical microfluidic chip arrangement 1000.

Figure 12A:
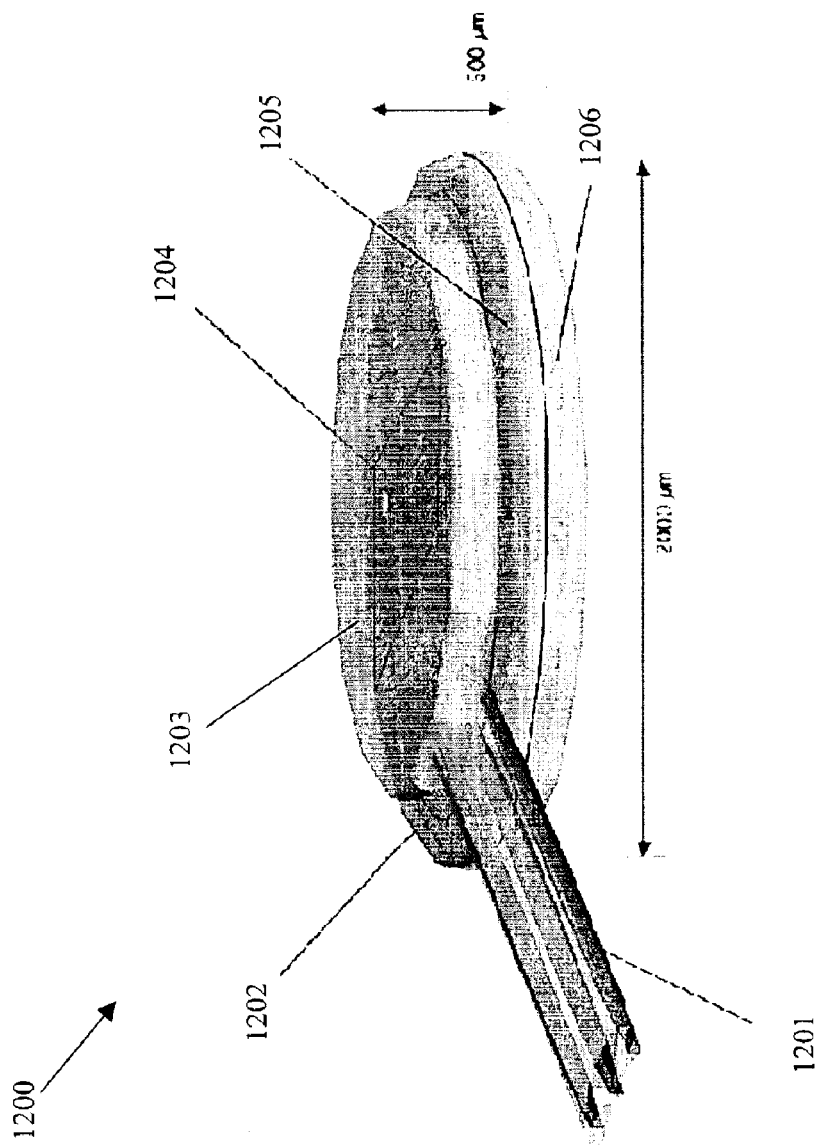
FIG. 12A shows a schematic view of a combined waveguide/microfluidic delivery system.

FIG. 12A shows a schematic view of a combined waveguide/microfluidic delivery system 1200, including an optical ultraviolet (UV) image pipe, fluid, and electrical input arrangement 1201, a four (4) level electro-optical microfluidic chip arrangement 1202, a waveguide structure 1203, an ultraviolet (UV) image reflector 1204, light collimating channels 1205, and microfluidic channels 1206.

Figure 12B:
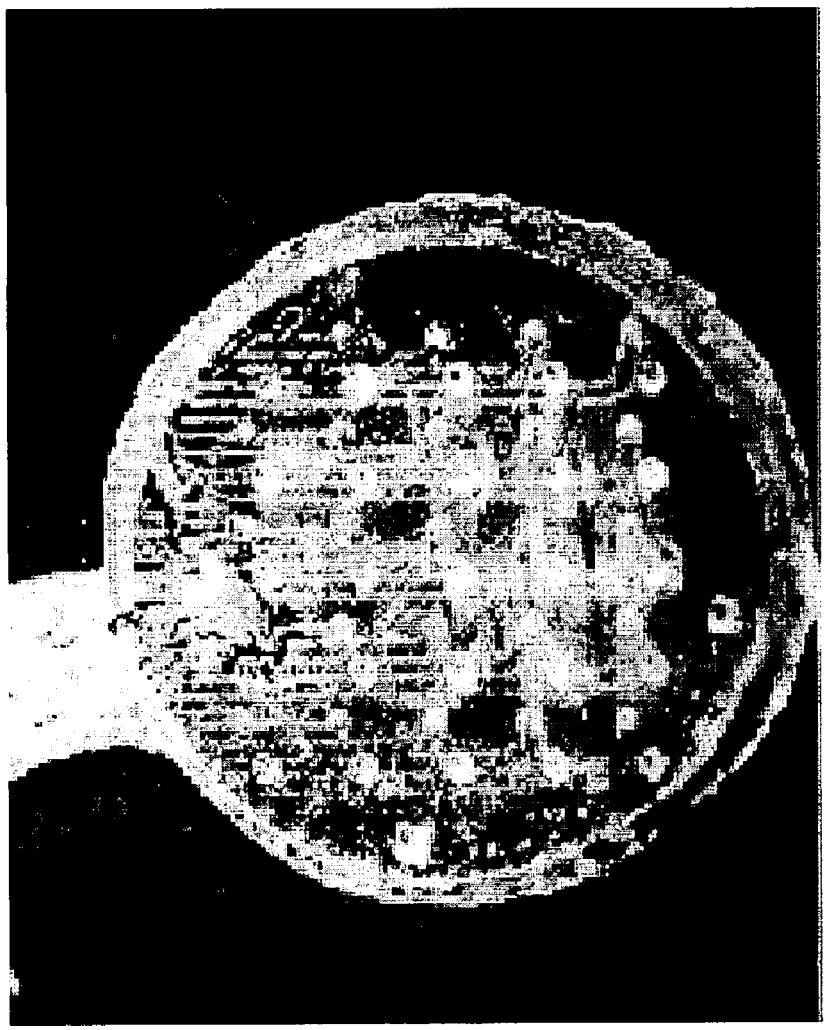
FIG. 12B shows an example embodiment of the combined waveguide/microfluidic delivery system.

FIG. 12B shows a combined waveguide/microfluidic delivery system. To fabricate the microfluidic chip, fluid holes may be ablated into, for example, approximately 200 μm thick glass so that the chip matches the geometry of the waveguide structure and is sealed at an offset of approximately 10 degrees to the waveguide. A fiber bundle of deep UV 50 μm core fiber optics may be carefully aligned to the microfluidic drug delivery chip package and sealed. Caged neurotransmitters may pass through 170 μm capillary tubing, and ultraviolet (UV) light may be coupled to the fiber bundle and guided through the waveguide to the offset fluid holes. The "cage" portion of the neurotransmitter may be cleaved off by the absorption of energy/photons within the waveguide structure.

Figure 13:
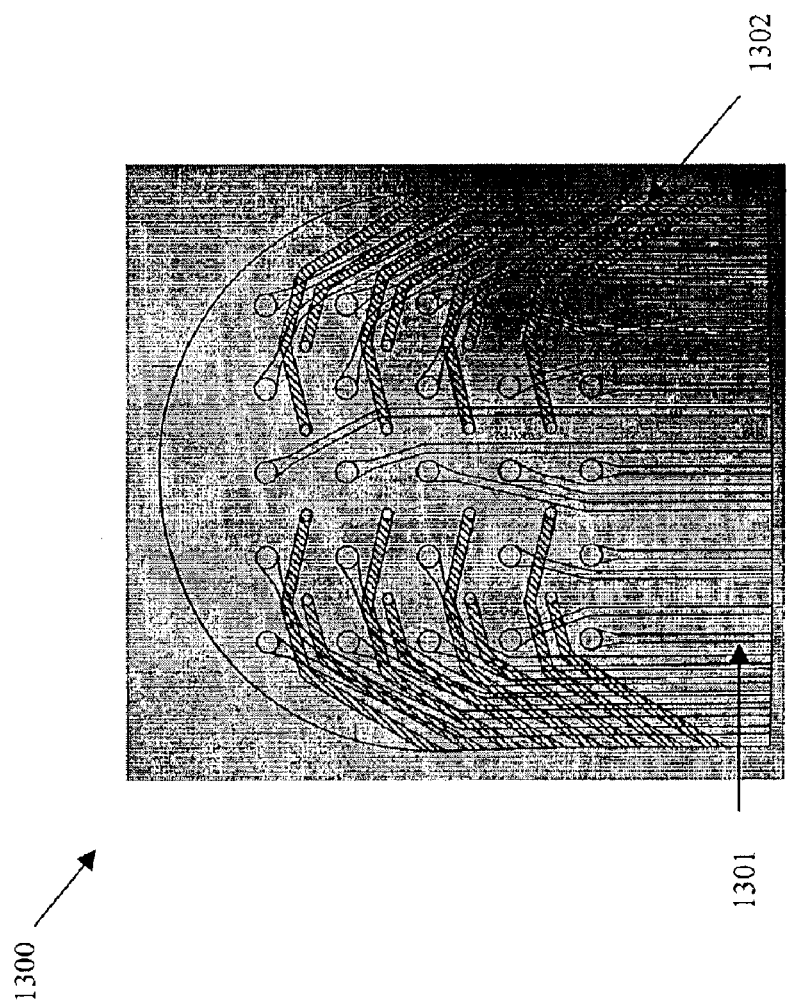
FIG. 13 shows an alternative exemplary geometry for waveguide structures and/or microfluidic delivery systems.

FIG. 13 shows an alternative exemplary geometry 1300 for waveguide and/or microfluidic delivery systems. The exemplary geometry 1300 provides, for example, an exemplary placement arrangement 1301 for a microfluidic channel 1301 and an exemplary placement arrangement for a metallized layer/electrode 1302. It is believed that an arranging the waveguide channels in a pentagon may accommodate a more densely packed geometry.

Figure 14:
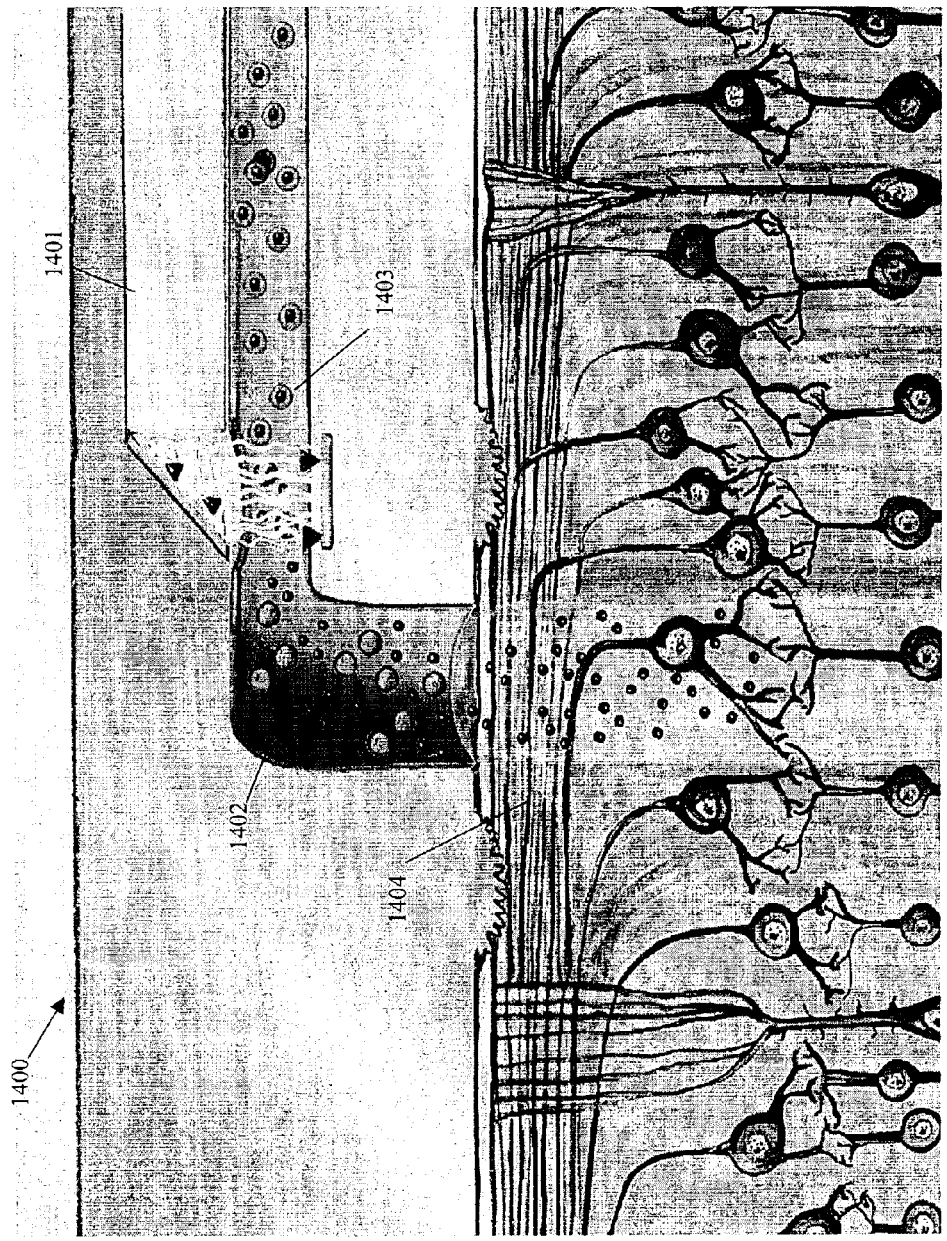
FIG. 14 shows an exemplary operation of a combined waveguide/microfluidic delivery system.

FIG. 14 shows an exemplary operation of a combined waveguide/microfluidic delivery system 1400, which includes a waveguide structure 1401 and a microfluidic channel 1402 so that light (for example, ultraviolet light) is guided into the microfluidic channel 1402 to uncage the caged molecules 1403 traveling in the microfluidic channel 1402 before they are delivered to neurological tissue 1404.

What is claimed is:

1. A waveguide structure for transmitting broad spectrum light, comprising:
   a wide bandgap semiconductor thin film arranged on a substrate and ablated to form a waveguide channel to transmit the broad spectrum light.

2. The waveguide structure of claim 1, wherein the broad spectrum light includes ultraviolet light and infrared light.

3. The waveguide structure of claim 1, wherein the broad spectrum light includes light with a range of 5 microns to 750 nanometers.

4. The waveguide structure of claim 1, wherein the wide bandgap semiconductor thin film includes aluminum nitride and the substrate includes sapphire.

5. The waveguide structure of claim 1, wherein the waveguide channel is approximately 5 μm to 50 μm wide.

6. The waveguide structure of claim 1, further comprising:
   a termination hole for the light to exit the waveguide structure.

7. The waveguide structure of claim 6, further comprising:
   a pixelated array of termination holes to direct the broad spectrum light.

8. A waveguide structure for transmitting broad spectrum light for use with a physiological delivery system, comprising:
   a wide bandgap semiconductor thin film arranged on a substrate and ablated to form a waveguide channel to transmit the broad spectrum light;
   wherein the waveguide structure is integrated with the physiological drug delivery system.

9. The waveguide structure of claim 8, wherein the physiological drug delivery system includes a microfluidic retinal prosthesis.

10. A waveguide structure for transmitting broad spectrum light for use with a miniaturized spectrometer system, comprising:
    a wide bandgap semiconductor thin film arranged on a substrate and ablated to form a waveguide channel to transmit the broad spectrum light;
    wherein the waveguide structure is arranged to transmit light to the miniaturized spectrometer system.

* * * * *

UNITED STATES PATENT AND TRADEMARK OFFICE
CERTIFICATE OF CORRECTION

PATENT NO.        : 7,043,129 B2                                       Page 1 of 1
APPLICATION NO.   : 10/353757
DATED             : May 9, 2006
INVENTOR(S)       : Gregory W. Auner et al.

It is certified that error appears in the above-identified patent and that said Letters Patent is hereby corrected as shown below:

Column 1, line 20, please insert:

--FEDERAL FUNDING

This invention was made with government support under grant/contract number DGE9870720 awarded by the National Science Foundation. The government has certain rights to the invention.--

Signed and Sealed this

Fourteenth Day of July, 2009

JOHN DOLL
*Acting Director of the United States Patent and Trademark Office*